United States Patent
Thirumalai Rajan et al.

(10) Patent No.: US 10,633,372 B2
(45) Date of Patent: Apr. 28, 2020

(54) PROCESS FOR THE PREPARATION OF AMORPHOUS (1S)-1,5-ANHYDRO-1-[3-[[5-(4 FLUOROPHENYL)-2-THIENYL]-4-METHYLPHENYL]-D-GLUCITOL AND ITS POLYMORPHS THEREOF

(71) Applicant: MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Chakilam Nagaraju, Telangana (IN); Achampeta Kodanda Ramprasad, Telangana (IN); Peri Seetha Rama Sarma, Telangana (IN); Boge Rajesham, Telangana (IN)

(73) Assignee: MSN LABORATORIES PRIVATE LIMITED, Hyderabad (IN)

( * ) Notice: Subject to any disclaimer, the term of this patent is extended or adjusted under 35 U.S.C. 154(b) by 3 days.

(21) Appl. No.: 15/553,843

(22) PCT Filed: Feb. 26, 2016

(86) PCT No.: PCT/IN2016/000053
§ 371 (c)(1),
(2) Date: Aug. 25, 2017

(87) PCT Pub. No.: WO2016/135747
PCT Pub. Date: Sep. 1, 2016

(65) Prior Publication Data
US 2018/0244661 A1    Aug. 30, 2018

(30) Foreign Application Priority Data

Feb. 27, 2015 (IN) .............................. 946/CHE/2015
May 5, 2015 (IN) .............................. 2265/CHE/2015
May 29, 2015 (IN) .............................. 2699/CHE/2015
Dec. 11, 2015 (IN) .............................. 6891/CHE/2015

(51) Int. Cl.
*C07D 409/10* (2006.01)
*A61K 9/14* (2006.01)

(52) U.S. Cl.
CPC ............ *C07D 409/10* (2013.01); *A61K 9/146* (2013.01); *C07B 2200/13* (2013.01)

(58) Field of Classification Search
CPC combination set(s) only.
See application file for complete search history.

(56) References Cited

U.S. PATENT DOCUMENTS

| 2016/0083374 A1* | 3/2016 | Dwivedi | C07D 409/10 514/23 |
| 2017/0145000 A1* | 5/2017 | Sheng | C07D 409/10 |
| 2018/0327395 A1* | 11/2018 | Zezula | B01D 9/0054 |

FOREIGN PATENT DOCUMENTS

| WO | WO-2005012326 A1 * | 2/2005 | C07H 19/048 |
| WO | WO-2010043682 A2 * | 4/2010 | C07D 333/12 |
| WO | WO 2011/079772 | 7/2011 | |
| WO | WO 2014/195966 | 12/2014 | |

OTHER PUBLICATIONS

Written Opinion of the International Searching Authority issued in International Patent Application No. PCT/IN2016/000053, dated Jul. 19, 2016.
International Search Report issued in International Patent Application No. PCT/IN2016/000053, dated Jul. 19, 2016.

* cited by examiner

*Primary Examiner* — Amanda L Aguirre
(74) *Attorney, Agent, or Firm* — IP Pundit LLC

(57) ABSTRACT

The present invention relates to an improved process for the preparation of amorphous (1S)-1,5-anhydro-1-[3-[[5-(4-fluorophenyl)-2-thienyl]methyl]-4-methylphenyl]-D-glucitol compound of formula-1, represented by the following structural formula.

Formula-1

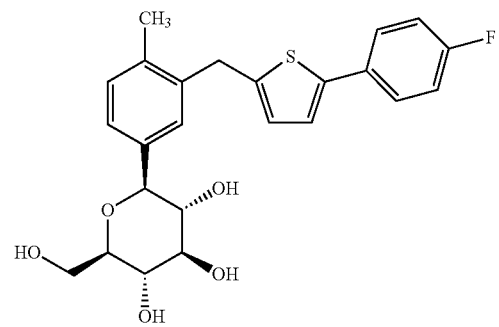

11 Claims, 4 Drawing Sheets

PROCESS FOR THE PREPARATION OF AMORPHOUS (1S)-1,5-ANHYDRO-1-[3-[[5-(4 FLUOROPHENYL)-2-THIENYL]-4-METHYLPHENYL]-D-GLUCITOL AND ITS POLYMORPHS THEREOF

RELATED APPLICATIONS

This application is a national phase application under 35 U.S.C. § 371 of International Application No. PCT/IN2016/000053, filed on Feb. 26, 2016, which claims priority to Indian patent application numbers 946/CHE/2015 filed on Feb 27, 2015, 2265/CHE/2015 filed on May 05, 2015, 2699/CHE/2015 filed on May 29, 2015 and 6891/CHE/2015 filed on Dec. 11, 2015; the disclosures of all of which are hereby incorporated by reference in their entirety.

FIELD OF THE INVENTION

The present invention relates to an improved process for the preparation of (1S)-1,5-anhydro-1-[3-[[5-(4-fluorophenyl)-2-thienyl]methyl]-4-methylphenyl]-D-glucitol compound of formula-1, represented by the following structural formula:

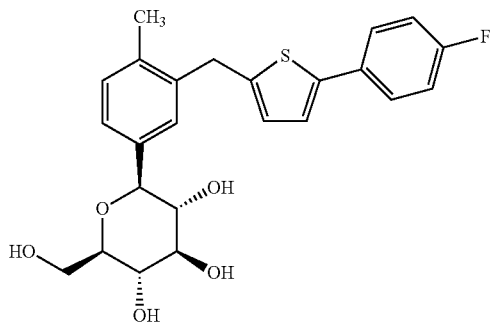

Formula-1

The present invention also relates to novel crystalline form and amorphous solid dispersion of (1S)-1,5-anhydro-1-[3-[[5-(4-fluorophenyl)-2-thienyl]methyl]-4-methyl phenyl]-D-glucitol compound of formula-1 and its process for the preparation.

Further, the present invention relates to an improved process for, the preparation of amorphous (1S)-1,5-anhydro-1-[3-[[5-(4-fluorophenyl)-2-thienyl]methyl]-4-methylphenyl]-D-glucitol compound of formula-1.

BACKGROUND OF THE INVENTION (1S)-1,5-anhydro-1-[3-[[5-(4-fluorophenyl)-2-thienyl] methyl]-4-methylphenyl]-D-glucitol, also known as Canagliflozin, belongs to a novel therapeutic class of sodium-glucose co-transporter 2 inhibitors. US drug regulatory approval was received in march 2013 for canagliflozin (INVOKANA™) as an adjunct to diet and exercise to improve glycemic control in adults with type-2 diabetes mellitus.

U.S. Pat. No. 7,943,788 B2 first discloses canagliflozin or salts thereof and the process for its preparation.

U.S. Pat. No. 7,943,582 B2 (herein after referred as US'582) and U.S. Pat. No. 8,513,202 B2 (herein after referred as US'202) discloses crystalline form of canagliflozin hemihydrate and process for preparation thereof.

US Publication No. 2013/0237487 A1 (herein after referred as US'487 A1) discloses amorphous dapagliflozin and amorphous canagliflozin. The US'487 A1 also discloses 1:1 crystalline complex of canagliflozin with L-proline (Form CS1), ethanol solvate of a 1:1 crystalline complex of canagliflozin with D-proline (Form CS2), 1:1 crystalline complex of canagliflozin with L-phenylalanine (Form CS3), 1:1 crystalline complex of canagliflozin with D-proline (Form CS4).

The US'487 A1 discloses preparation of amorphous canagliflozin by adding toluene solution into n-heptane. After drying in vacuo the product was obtained as a white solid with melting point of 54.7° C. to 72.0° C. However, upon repetition of the said experiment, the obtained amorphous canagliflozin was having higher amount of residual solvents. Therefore, the amorphous canagliflozin obtained by process as disclosed in US'487 A1 is not suitable for pharmaceutical preparations.

The US'487 A1 further discloses that amorphous canagliflozin obtained by the above process is hygroscopic in nature which was confirmed by Dynamic vapor sorption (DVS) analysis. Further, it was observed that the amorphous form underwent a physical change between the sorption/desorption cycle, making the sorption/desorption behavior different between the two cycles. The physical change that occurred was determined to be a conversion or partial conversion from the amorphous state to a crystalline state. This change was supported by a change in the overall appearance of the sample as the humidity increased from 70% to 90% RH.

Furthermore, WO2008/069327 A1 mentions that amorphous (1S)-1,5-anhydro-1-[3-[[5-(4-fluorophenyl)-2-thienyl]methyl]-4-methylphenyl]-D-glucitol suffers from stability and handling issues such as poor filterability.

Therefore, it is evident from the prior art that the reported amorphous form of canagliflozin is unstable and hygroscopic as well as not suitable for pharmaceutical preparations due to higher amount of residual solvents above the ICH acceptable limits.

Hence, there is a need to provide a stable amorphous form of canagliflozin which is suitable for pharmaceutical preparations.

In view of the above, the present invention provides an improved process for the preparation of stable amorphous form of (1S)-1,5-anhydro-1-[3-[[5-(4-fluorophenyl)-2-thienyl]methyl]-4-methyl phenyl]-D-glucitol which is well suitable for the pharmaceutical preparation.

BRIEF DESCRIPTION OF THE INVENTION

The first aspect of the present invention is to provide a process for the preparation of amorphous form of (1S)-1,5-anhydro-1-[3-[[5-(4-fluorophenyl)-2-thienyl]methyl]-4-methyl phenyl]-D-glucitol compound of formula-1.

The second aspect of the present invention is to provide an improved process for the preparation of amorphous (1S)-1,5-anhydro-1-[3-[[5-(4-fluorophenyl)-2-thienyl] methyl]-4-methylphenyl]-D-glucitol compound of formula-1.

The third aspect of the present invention is to provide an alternate improved process for the preparation of (1S)-1,5-anhydro-1-[3-[[5-(4-fluorophenyl)-2-thienyl]methyl]-4-methyl phenyl]-D-glucitol compound of formula-1.

The fourth aspect of the present invention is to provide a process for the preparation of (2S,3R,4S,5S,6R)-2-(3-((5-

(4-fluorophenyl)thiophen-2-yl)methyl)-4-methylphenyl)-6-(hydroxylmethyl) tetrahydro-2H-pyran-2,3,4,5-tetraol compound of formula-5.

The fifth aspect of the present invention is to provide novel (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol compound of formula-5.

The sixth aspect of the present invention is to provide a process for the preparation of (1S)-1,5-anhydro-1-[3-[[5-(4-fluorophenyl)-2-thienyl]methyl]-4-methylphenyl]-D-glucitol compound of formula-1.

The seventh aspect of the present invention is to provide novel (2R,3R,4S,5R,6R)-6-(acetoxymethyl)-2-(3-((5-(4-fluorophenyl)thiophen-2-yl)methyl)-4-methylphenyl)tetrahydro-2H-pyran-2,3,4,5-tetrayltetraacetate compound of formula-11.

The eighth aspect of the present invention is to provide a process for the preparation of (1S)-1,5-anhydro-1-[3-[[5-(4-fluorophenyl)-2-thienyl]methyl]-4-methylphenyl]-D-glucitol compound of formula-1, comprising of reducing (2S,3R,4S,5S,6R)-2-(3-((5-(4-fluoro phenyl)thiophen-2-yl)methyl)-4-methylphenyl)-6-(hydroxymethyl)tetrahydro-2H-pyran-2,3,4,5-tetraol compound of formula-5 with a suitable reducing agent in a suitable solvent to provide compound of formula-1.

The ninth aspect of the present invention is to provide a crystalline form of (2S,3R,4S,5S,6R)-2-(3-((5-(4-fluorophenyl)thiophen-2-yl)methyl)-4-methylphenyl)-6-(hydroxylmethyl)tetrahydro-2H-pyran-2,3,4,5-tetraol compound of formula-5.

The tenth aspect of the present invention is to provide a process for the preparation of amorphous (1S)-1,5-anhydro-1-[3-[[5-(4-fluorophenyl)-2-thienyl]methyl]-4-methylphenyl]-D-glucitol compound of formula-1.

The eleventh aspect of the present invention is to provide a novel crystalline form of (1S)-1,5-anhydro-1-[3-[[5-(4-fluorophenyl)-2-thienyl]methyl]-4-methylphenyl]-D-glucitol compound of formula-1 herein after designated as form-M.

The twelfth aspect of the present invention is to provide a process for the preparation of crystalline form-M of (1S)-1,5-anhydro-1-[3-[[5-(4-fluorophenyl)-2-thienyl]methyl]-4-methylphenyl]-D-glucitol compound of formula-1.

The thirteenth aspect of the present invention is to provide amorphous solid dispersion of (1S)-1,5-anhydro-1-[3-[[5-(4-fluorophenyl)-2-thienyl]methyl]-4-methyl phenyl]-D-glucitol compound of formula-1 with one or more pharmaceutical acceptable carrier.

The fourteenth aspect of the present invention is to provide a process for the preparation of amorphous solid dispersion of (1S)-1,5-anhydro-1-[3-[[5-(4-fluorophenyl)-2-thienyl] methyl]-4-methylphenyl]-D-glucitol compound of formula-1 in combination with one or more pharmaceutical acceptable carrier.

DETAILED DESCRIPTION OF THE INVENTION

Figure 1:
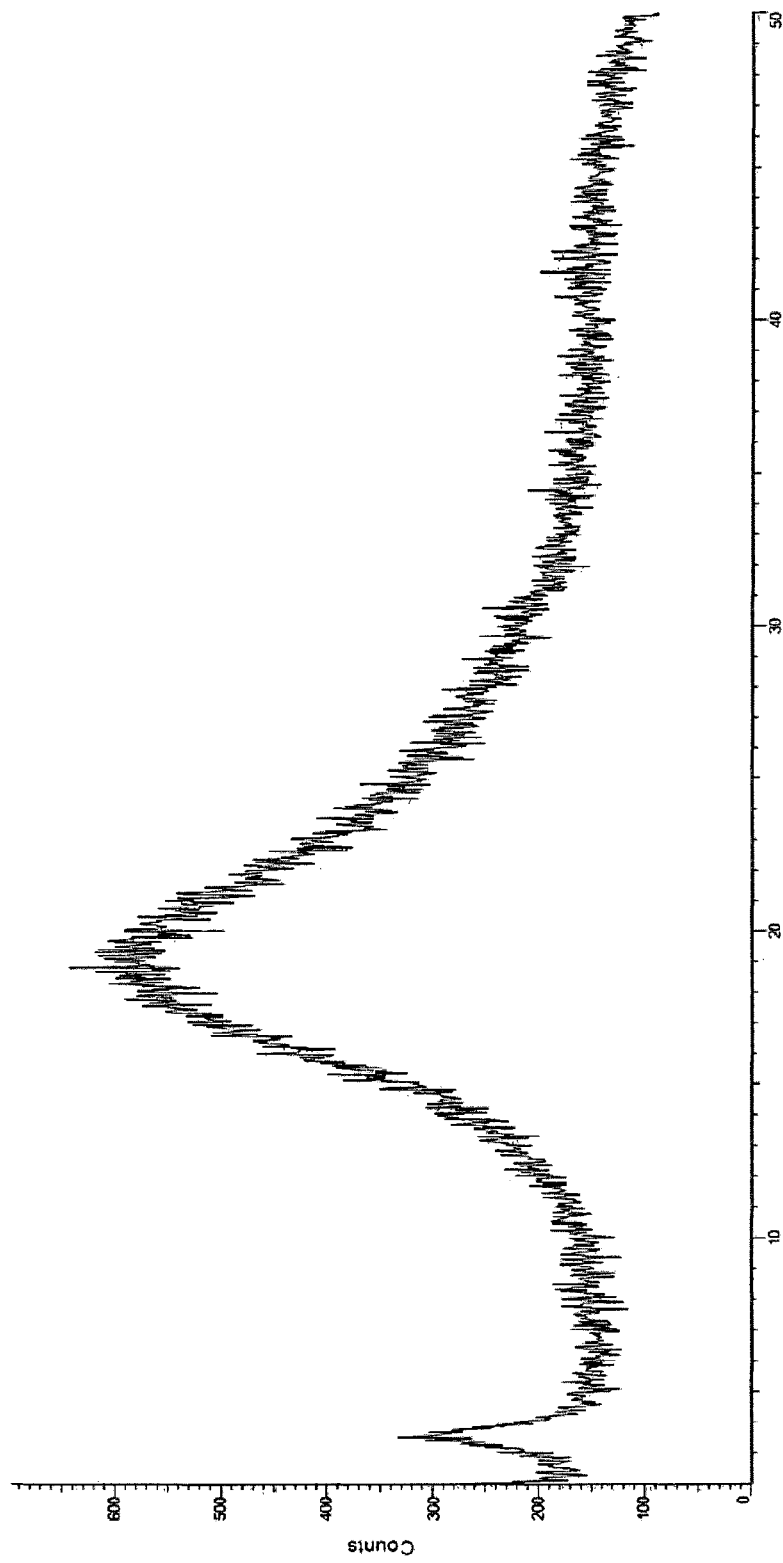
FIG. 1: Illustrates the PXRD pattern of amorphous form of (1S)-1,5-anhydro-1-[3-[[5-(4-fluorophenyl)-2-thienyl] methyl]-4-methylphenyl]-D-glucitol compound of formula-1.
Figure 2:
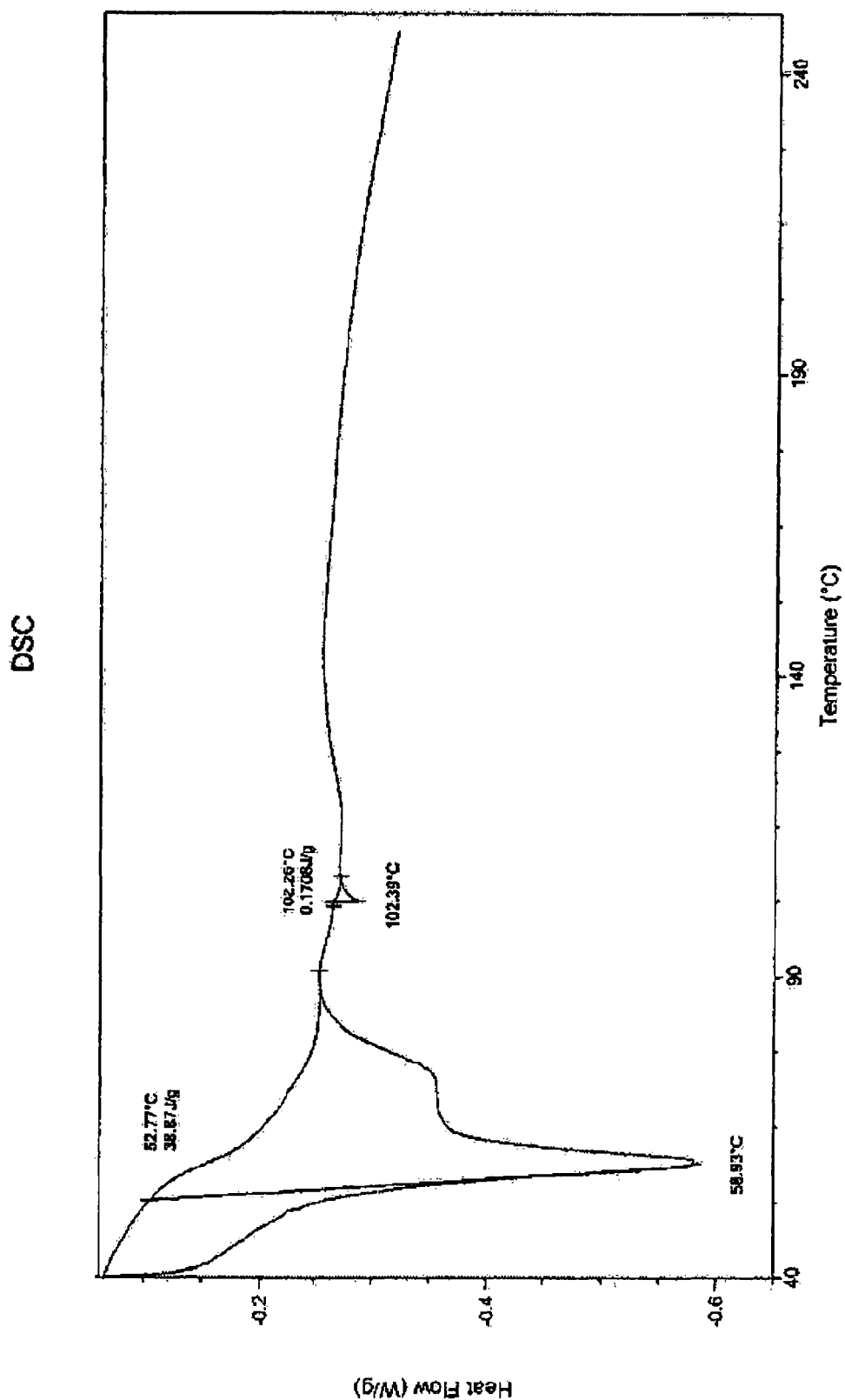
FIG. 2: Illustrates the DSC thermogram of amorphous form of (1S)-1,5-anhydro-1-[3-[[5-(4-fluorophenyl)-2-thienyl]methyl]-4-methylphenyl]-D-glucitol compound of formula-1.

The present invention provides a process for the preparation of amorphous form of (1S)-1,5-anhydro-1-[3-[[5-(4-fluorophenyl)-2-thienyl]methyl]-4-methylphenyl]-D-glucitol compound of formula-1.

As used herein the term "suitable solvent" used in the present invention refers to "hydrocarbon solvents" such as n-hexane, n-heptane, cyclohexane, pet ether, toluene, pentane, cycloheptane, methylcyclohexane, m-, o-, or p-xylene, and the like; "ether solvents" such as dimethoxy methane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethylacetamide (DMA), dimethylformamide (DMF), dimethyl sulfoxide (DMSO), N-methylpyrrolidone (NMP) and the like; "chloro solvents" such as dichloro methane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 2-methoxyethanol, 1, 2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia, methanolic ammonia; and organic bases such as triethyl amine, methyl amine, ethyl amine, 1,8-Diazabicyclo[5.4.0]undec-7-ene (DBU), 1,5-Diazabicyclo (4.3.0)non-5-ene (DBN), lithium dioisoporpylamide (LDA), n-butyl lithium, tribenzylamine, isopropyl amine, diisopropylamine, diisopropylethylamine, N-methylmorpholine, N-ethylmorpholine, piperidine, dimethyl amino pyridine, morpholine, pyridine, 2,6-lutidine, 2,4,6-collidine, imidazole, 1-methylimidazole, 1,2,4-triazole, 1,4-diazabicyclo [2.2.2]octane (DABCO) or mixtures thereof.

As used herein the term suitable "chlorinating agent" include but are not limited to chlorine, oxalyl chloride, sulfuryl chloride, thionyl chloride, phosphorus oxychloride, phosphorus pentachloride, pivaloyl chloride, antimony pentachloride, iodine trichloride, sulfur dichloride, manganese tetra chloride and the like.

As used herein the term suitable "Lewi's acid" is selected from aluminium chloride, boran trichloride, ferric chloride, tin tetrachloride, stibium penta chloride and TiCl$_4$.

As used herein the term suitable "pharmaceutical acceptable carrier" is preferably a polymeric carrier, and more preferably is at least one from the group consisting of starches, modified starches, cellulose, methyl cellulose (MC), ethyl cellulose (EC), hydroxyethyl cellulose (HEC), hydroxypropyl cellulose (HPC), hydroxypropylmethyl cellulose (HPMC), polycarbophil, polyethylene glycol (PEG), polyethylene oxides, polyoxyalkylene derivatives, polymethacrylates, polyvinyl pyrrolidone (PVP), polyvinyl acetate (PVAc), PVP-vinylacetate-copolymer (PVP-VA), Kollidon® VA 64 (a vinylpyrrolidone-vinyl acetate copolymer), lactose, sorbitol, mannitol, maltitol, saccharose, isomalt, cyclodextrins such as cc-cyclodextrins, β-cyclodextrins, γ-cyclodextrins, hydroxyl-propyl-cyclodextrins, hydroxypropyl-cyclodextrin (HρβOὑ), sodium carboxymethyl cellulose cross-linked polyacrylic acid (carbipol), or a mixture thereof.

The first aspect of the present invention provides a process for the preparation of amorphous form of (1S)-1,5-anhydro-1-[3-[[5-(4-fluorophenyl)-2-thienyl]methyl]-4-methyl phenyl]-D-glucitol compound of formula-1, comprising of the following steps:
  a) Treating (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyltriacetate compound of formula-6 with a suitable base in a suitable solvent,
  b) absorbing the obtained compound on silica gel or silicon dioxide or neutral alumina in a suitable solvent,
  c) adding a suitable solvent or mixture of solvents to the compound obtained in step-b),
  d) filtering the solid,
  e) adding a suitable solvent to the compound obtained in step-d) and heating the reaction mixture,
  f) stirring and filtering the reaction mixture,
  g) adding a suitable solvent to the filtrate obtained in step-f),
  h) optionally, treating the reaction mixture with carbon,
  i) distilling off the solvent completely from the reaction mixture obtained in step-g) or step-h) to provide amorphous (1S)-1,5-anhydro-1-[3-[[5-(4-fluorophenyl)-2-thienyl] methyl]-4-methylphenyl]-D-glucitol compound of formula-1.

Wherein,
in step-a) the suitable base is selected from organic or inorganic base; preferably inorganic base;
in step-a), b), c), e) and g) the suitable solvent is selected from alcohol solvents, ether solvents, chloro solvents, ketone solvents, ester solvents, hydrocarbon solvents, polar aprotic solvents and polar solvents like water or mixture thereof.

The preferred embodiment of the present invention provides a process for the preparation of amorphous form of (1S)-1,5-anhydro-1-[3-[[5-(4-fluorophenyl)-2-thienyl] methyl]-4-methyl phenyl]-D-glucitol compound of formula-1, comprising of the following steps:
  a) Treating (2R,3R,4R,5S,6S)-2-(acetoxymethyl)-6-(3-((5-(4-fluorophenyl)thiophen-2-yl) methyl)-4-methylphenyl)tetrahydro-2H-pyran-3,4,5-triyltriacetate compound of formula-6 with sodium carbonate in methanol,
  b) absorbing the obtained compound on silica gel in dichloromethane,
  c) adding a mixture of methanol and water to the compound obtained in step-b),
  d) filtering the solid,
  e) adding dichloromethane to the compound obtained in step-d) and heating the reaction mixture,
  f) stirring and filtering the reaction mixture optionally using hy-flow,
  g) adding ethyl acetate to the filtrate obtained in step-f),
  h) adding charcoal to the reaction mixture,
  i) filtering the reaction mixture,
  j) distilling off the solvent completely from the filtrate obtained in step-i) to provide amorphous (1S)-1,5-anhydro-1-[3-[[5-(4-fluorophenyl)-2-thienyl]methyl]-4-methyl phenyl]-D-glucitol compound of formula-1.

In another preferred embodiment of the present invention provides a process for the preparation of amorphous form of (1S)-1,5-anhydro-1-[3-[[5-(4-fluorophenyl)-2-thienyl] methyl]-4-methyl phenyl]-D-glucitol compound of formula-1, comprising of the following steps:
  a) Treating (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyltriacetate compound of formula-6 with sodium carbonate in methanol,
  b) absorbing the obtained compound on silica gel in dichloromethane,
  c) adding methanol to the compound obtained in step-b),
  d) stirring the reaction mixture,
  e) adding water and stirring the reaction mixture,
  f) filtering the solid,
  g) adding dichloromethane to the compound obtained in step-f) and heating the reaction mixture,
  h) stirring and filtering the reaction mixture,
  i) adding ethyl acetate to the filtrate obtained in step-h),
  j) adding charcoal to the reaction mixture,
  k) filtering the reaction mixture,
  l) distilling off the solvent completely from the filtrate obtained in step-k) to provide amorphous (1S)-1,5-anhydro-1-[3-[[5-(4-fluorophenyl)-2-thienyl]methyl]-4-methyl phenyl]-D-glucitol compound of formula-1.

The powder X-ray diffractogram of amorphous form of (1S)-1,5-anhydro-1-[3-[[5-(4-fluorophenyl)-2-thienyl] methyl]-4-methylphenyl]-D-glucitol compound of formula-1 obtained according to the present invention was depicted in FIG. 1.

Further, (1S)-1,5-anhydro-1-[3-[[5-(4-fluorophenyl)-2-thienyl]methyl]-4-methyl phenyl]-D-glucitol compound of formula-1 of the present invention is having purity greater than 99% as measured by HPLC and residual solvents less than 0.05%.

The second aspect of the present invention provides an improved process for the preparation of amorphous (1S)-1,5-anhydro-1-[3-[[5-(4-fluorophenyl)-2-thienyl]methyl]-4-methylphenyl]-D-glucitol compound of formula-1, comprising of the following steps:
  a) Reacting (3R,4S,5S,6R)-3,4,5-trihydroxy-6-(hydroxymethyl)tetrahydro-2H-pyran-2-one compound of formula-2 with trimethyl silyl chloride in presence of a suitable base in a suitable solvent to provide (3R,4S,5S,6R)-3,4,5-tris(trimethylsilyloxy)-6-((trimethyl silyloxy)methyl)tetrahydro-2H-pyran-2-one compound of formula-3, b) reacting (3R,4S,5R,6R)-3,4,5-tris(trimethylsilyloxy)-6-((trimethylsilyloxy)methyl) tetrahydro-2H-pyran-2-one compound of formula-3 with 2-(4-fluorophenyl)-5-(5-iodo-2-methylbenzyl)thiophene compound of formula-4 in presence of n-butyl lithium in a suitable solvent, at a temperature ranging from about −78° C. to 0° C. to provide (2S,3R,4S,5S,6R)-2-(3-((5-(4-fluorophenyl)thiophen-2-yl)methyl)-4-methylphenyl)-6-(hydroxymethyl) tetrahydro-2H-pyran-2,3,4,5-tetraol compound of formula-5; wherein the n-butyl lithium is added to a mixture of the compound of formula-3 and the compound of formula-4, c) reducing the compound of formula-5 with a suitable reducing agent in a suitable solvent to provide (1S)-1,5-anhydro-1-[3-[[5-(4-fluorophenyl)-2-thienyl]methyl]-4-methyl phenyl]-D-glucitol compound of formula-1, d) acetylating the compound of formula-1 with a suitable acetylating agent in presence of a suitable base in a suitable solvent to provide (2R,3R,4R,5S,6S)-2-(acetoxy methyl)-6-(3-((5-(4-fluorophenyl)thiophen-2-yl)methyl)-4-methylphenyl)tetrahydro-2H-pyran-3,4,5-triyltriacetate compound of formula-6, e) treating the compound of formula-6 with a suitable base in a suitable solvent to provide (1S)-1,5-anhydro-1-[3-[[5-(4-fluorophenyl)-2-thienyl]methyl]-4-methyl phenyl]-D-glucitol compound of formula-1, f) absorbing the compound of formula-1 obtained compound on silica gel or silicon dioxide or neutral alumina in presence of a suitable solvent, g) adding a suitable solvent to the compound obtained in step-f), h) stirring the reaction mixture, i) adding a suitable solvent and stirring the reaction mixture, j) filtering the solid, k) adding a suitable solvent to the compound obtained in step-j) and heating the reaction mixture, l) stirring and filtering the reaction mixture.

m) adding a suitable solvent to the filtrate obtained in step-l), n) optionally, treating the reaction mixture with carbon, o) distilling off the solvent completely from the reaction mixture obtained in step-m) or step-n) to provide amorphous (1S)-1,5-anhydro-1-[3-[[5-(4-fluorophenyl)-2-thienyl] methyl]-4-methylphenyl]-D-glucitol compound of formula-1.

Wherein, in step-a), d) and e) the suitable base is selected from organic or inorganic base;

in step b) n-butyl lithium is used at least 1.0 mole equivalents and at most 4.0 mole equivalents w.r.to compound of formula-3.

in step-c) the suitable reducing agent is selected from trialkyl silanes such as trimethyl silane, triethylsilane optionally in combination with a suitable lewi's acid or trifluoroacetic acid or $BF_3$-etherate; trichlorosilane, sodium borohydride optionally in combination with BF3-etherate, diborane, potassium borohydride, sodium cyanoborohydride, lithium borohydride, lithium aluminium hydride, diisobutylaluminium hydride (DIBAL-H), lithium triethylborohydride ($LiEt_3BH$), L-selectride, sodium bis(2-methoxyethoxy)aluminium hydride (vitride), sodium borohydride/$BF_3$-etherate, sodium boro hydride/aluminium chloride, borane/aluminium chloride, sodium borohydride/iodine, Trifluoroacetic acid/sodium 30 borohydride, Zn—Hg, sodium borohydride/tosylhydrazone, 9-BBN and the like;

in step-d) the suitable acetylating agent is selected from acetic anhydride or acetyl chloride;

in step-a), b), c), d), e), f), g), i), k) and m) the suitable solvent is selected from alcohol solvents, ether solvents, chloro solvents, ketone solvents, ester solvents, hydrocarbon solvents, polar aprotic solvents and polar solvents like water or mixture thereof.

The preferred embodiment of the present invention provides an improved process for the preparation of amorphous (1S)-1,5-anhydro-1-[3-[[5-(4-fluorophenyl)-2-thienyl] methyl]-4-methylphenyl]-D-glucitol compound of formula-1, comprising of the following steps:

a) Reacting (3R,4S,5S,6R)-3,4,5-trihydroxy-6-(hydroxymethyl)tetrahydro-2H-pyran-2-one compound of formula-2 with trimethyl silyl chloride in presence of a n-methyl morpholine in tetrahydrofuran to provide (3R,4S,5R,6R)-3,4,5-tris(trimethylsilyloxy)-6-((trimethylsilyloxy) methyl)tetrahydro-2H-pyran-2-one compound of formula-3, b) reacting (3R,4S,5R,6R)-3,4,5-tris(trimethylsilyloxy)-6-((trimethylsilyloxy)methyl) tetrahydro-2H-pyran-2-one compound of formula-3 with 2-(4-fluorophenyl)-5-(5-iodo-2-methylbenzyl)thiophene compound of formula-4 in presence of at least 1.0 mole equivalents and at most 4.0 mole equivalents of n-butyl lithium w.r.to compound of formula-3 in tetrahydrofuran at a temperature ranging from about −78° C. to 0° C. to provide (2S,3R,4S,5S,6R)-2-(3-((5-(4-fluorophenyl)thiophen-2-yl)methyl)-4-methyl phenyl)-6-(hydroxymethyl)tetrahydro-2H-pyran-2,3,4,5-tetraol compound of formula-5, wherein the n-butyl lithium is added to a mixture of the compound of formula-3 and the compound of formula-4 c) reducing the compound of formula-5 with triethylsilane/ BF3-etherate in dichloromethane to provide (1S)-1,5-anhydro-1-[3-[[5-(4-fluorophenyl)-2-thienyl] methyl]-4-methyl phenyl]-D-glucitol compound of formula-1, d) acetylating the compound of formula-1 with acetic anhydride in presence of dimethylamino pyridine in dichloromethane to provide (2R,3R,4R,5S,6S)-2-(acetoxy methyl)-6-(3-((5-(4-fluorophenyl)thiophen-2-yl)methyl)-4-methylphenyl) tetrahydro-2H-pyran-3,4,5-triylttriacetate compound of formula-6, e) treating the compound of formula-6 with sodium carbonate in methanol to provide (1S)-1,5-anhydro-1-[3-[[5-(4-fluorophenyl)-2-thienyl]methyl]-4-methylphenyl]-D-glucitol compound of formula-1, f) absorbing the compound of formula-1 on silica gel in presence of dichloromethane, g) adding methanol to the compound obtained in step-f), h) stirring the reaction mixture, i) adding a water and stirring the reaction mixture, j) filtering the reaction mixture, k) adding a dichloromethane to the compound obtained in step-j) and heating the reaction mixture, l) stirring and filtering the reaction mixture, m) adding ethyl acetate to the filtrate obtained in step-1), n) adding charcoal to the reaction mixture, o) filtering the reaction mixture, p) distilling off the solvent completely from the filtrate obtained in step-o) to provide amorphous (1S)-1,5-anhydro-1-[3-[[5-(4-fluorophenyl)-2-thienyl]methyl]-4-methyl phenyl]-D-glucitol compound of formula-1.

Amorphous form of canagliflozin of the present invention is substantially free from residual solvents. The term "substantially free" means residual solvents within the permissible ICH limits suitable for pharmaceutical preparations. For example but not limited to less than 0.5%, particularly less than 0.3% or more particularly less than 0.2%.

Amorphous (1S)-1,5-anhydro-1-[3-[[5-(4-fluorophenyl)-2-thienyl]methyl]-4-methyl phenyl]-D-glucitol compound of formula-1 obtained according to the present invention is free of crystalline forms.

The third aspect of the present invention provides an improved process for the preparation of (1S)-1,5-anhydro-1-[3-[[5-(4-fluorophenyl)-2-thienyl]methyl]-4-methyl phenyl]-D-glucitol compound of formula-1, comprising of the following steps:
a) Reacting 5-iodo-2-methylbenzoic acid compound of formula-7 with a suitable chlorinating agent in a suitable solvent to provide 5-iodo-2-methylbenzoyl chloride, which further reacts with 2-(4-fluorophenyl)thiophene compound of formula-8 in presence of Lewi's acid to provide (5-(4-fluorophenyl)thiophen-2-yl)(5-iodo-2-methylphenyl)methanone compound of formula-9,
b) reducing the compound of formula-9 with a suitable reducing agent in a suitable solvent to provide 2-(4-fluorophenyl)-5-(5-iodo-2-methylbenzyl)thiophene compound of formula-4,
c) reacting the compound of formula-4 with (3R,4S,5R,6R)-3,4,5-tris(trimethylsilyl oxy)-6-((trimethylsilyloxy)methyl)tetrahydro-2H-pyran-2-one compound of formula-3 in presence of methyl lithium in a suitable solvent to provide (2S,3R,4S,5R,6R)-2-(3-((5-(4-fluorophenyl)thiophen-2-yl) methyl)-4-methylphenyl)-3,4,5-tris(trimethylsilyloxy)-6-((trimethylsilyloxy)methyl) tetrahydro-2H-pyran-2-ol compound of formula-10,
d) reacting the compound of formula-10 in-situ with methane sulfonic acid in presence of a suitable base in a suitable solvent to provide (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol compound of formula-5,
e) reducing the compound of formula-5 in-situ with a suitable reducing agent in a suitable solvent to provide (1S)-1,5-anhydro-1-[3-[[5-(4-fluorophenyl)-2-thienyl] methyl]-4-methylphenyl]-D-glucitol compound of formula-1,
f) acetylating the compound of formula-1 with a suitable acetylating agent in presence of a suitable base in a suitable solvent to provide (2R,3R,4R,5S,6S)-2-(acetoxy methyl)-6-(3-((5-(4-fluorophenyl)thiophen-2-yl) methyl)-4-methylphenyl)tetrahydro-2H-pyran-3,4,5-triyltriacetate compound of formula-6,
g) optionally, purifying the compound of formula-6 using a suitable solvent,
h) reacting the compound of formula-6 with a suitable base in a suitable solvent to provide (1S)-1,5-anhydro-1-[3-[[5-(4-fluorophenyl)-2-thienyl]methyl]-4-methyl phenyl]-D-glucitol compound of formula-1.

Wherein,
in step-a) the suitable chlorinating agent is selected from chlorine, oxalyl chloride, sulfuryl chloride, thionyl chloride, phosphorus oxychloride, phosphorus pentachloride, pivaloyl chloride; the suitable lewi's acid is selected from aluminium chloride, boran trichloride, ferric chloride, tin tetrachloride;
in step-b) & e) the suitable reducing agent is selected from trialkyl silanes such as trimethyl silane, triethylsilane optionally in combination with a suitable lewi's acid or trifluoroacetic acid or BF$_3$-etherate; trichlorosilane, sodium borohydride optionally in combination with BF3-etherate, diborane, potassium borohydride, sodium cyanoborohydride, lithium borohydride, lithium aluminium hydride, diisobutylaluminium hydride (DIBAL-H), lithium triethylborohydride (LiEt$_3$BH), L-selectride, sodium bis(2-methoxyethoxy)aluminium hydride (vitride), sodium borohydride/BF$_3$-etherate, sodium boro hydride/aluminium chloride, borane/aluminium chloride, sodium borohydride/iodine, Trifluoroacetic acid/sodium borohydride, Zn—Hg, sodium borohydride/tosylhydrazone, 9-BBN and the like;
in step-d), f) & h) the suitable base is selected from organic (or) inorganic base;
in step-f) the suitable acetylating agent is selected from acetic anhydride or acetyl chloride;
in step-a) to step-h) the suitable solvent is selected from alcohol solvents, ether solvents, chloro solvents, ketone solvents, ester solvents, hydrocarbon solvents, polar aprotic solvents, polar solvents like water or mixture thereof.

The preferred embodiment of the present invention provides an improved process for the preparation of (1S)-1,5-anhydro-1-[3-[[5-(4-fluorophenyl)-2-thienyl]methyl]-4-methylphenyl]-D-glucitol compound of formula-1, comprising of the following steps:
a) Reacting 5-iodo-2-methylbenzoic acid compound of formula-7

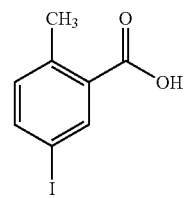

Formula-7 with thionyl chloride in a mixture of dimethyl formamide and dichloromethane to provide 5-iodo-2-methylbenzoyl chloride, which further reacts with 2-(4-fluorophenyl)thiophene compound of formula-8

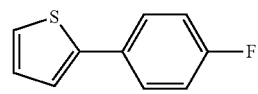

Formula-8 in presence of aluminum chloride provides (5-(4-fluorophenyl)thiophen-2-yl)(5-iodo-2-methylphenyl) methanone compound of formula-9,

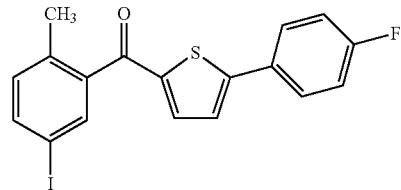

Formula-9 b) reducing the compound of formula-9 with triethylsilane/BF$_3$-etherate in presence of acetonitrile to provide 2-(4-fluorophenyl)-5-(5-iodo-2-methylbenzyl)thiophene compound of formula-4,
c) reacting the compound of formula-4 with (3R,4S,5R,6R)-3,4,5-tris(trimethyl silyloxy)-6-((trimethylsilyloxy)methyl)tetrahydro-2H-pyran-2-one compound of formula-3 in presence of methyl lithium in tetrahydrofuran to provide (2S,3R,4S,5R,6R)-2-(3-((5-(4-fluorophenyl)thiophen-2-yl)methyl)-4-methylphenyl)-3,4,5-tris(trimethylsilyloxy)-6-((trimethylsilyloxy)methyl) tetrahydro-2H-pyran-2-ol compound of formula-10, Formula-10

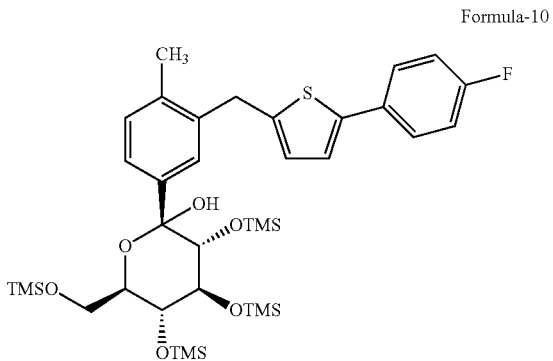

d) reacting the compound of formula-10 in-situ with methane sulfonic acid in presence of sodium bicarbonate in methanol to provide (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol compound of formula-5, e) reducing the compound of formula-5 in-situ with triethylsilane/BF3-etherate in dichloromethane to provide (1S)-1,5-anhydro-1-[3-[[5-(4-fluorophenyl)-2-thienyl] methyl]-4-methyl phenyl]-D-glucitol compound of formula-1, f) acetylating the compound of formula-1 with acetic anhydride in presence of dimethyl aminopyridine in dichloromethane to provide (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyltriacetate compound of formula-6, g) purifying the compound of formula-6 using a mixture of ethyl acetate and methanol, h) reacting the compound of formula-6 with sodium carbonate in aqueous methanol to provide (1S)-1,5-anhydro-1-[3-[[5-(4-fluorophenyl)-2-thienyl]methyl]-4-methyl phenyl]-D-glucitol compound of formula-1.

The fourth aspect of the present invention provides a process for the preparation of (2S,3R,4S,5S,6R)-2-(3-((5-(4-fluorophenyl)thiophen-2-yl)methyl)-4-methylphenyl)-6-(hydroxymethyl) tetrahydro-2H-pyran-2,3,4,5-tetraol compound of formula-5, comprising of the following steps:

a) Reacting the 2-(4-fluorophenyl)-5-(5-iodo-2-methylbenzyl)thiophene compound of formula-4 with (3R,4S,5R,6R)-3,4,5-tris(trimethylsilyloxy)-6-((trimethylsilyloxy) methyl)tetrahydro-2H-pyran-2-one compound of formula-3 in presence of methyl lithium in a suitable solvent to provide (2S,3R,4S,5R,6R)-2-(3-((5-(4-fluorophenyl)thiophen-2-yl)methyl)-4-methylphenyl)-3,4,5-tris(trimethylsilyloxy)-6-((trimethylsilyloxy)methyl) tetrahydro-2H-pyran-2-ol compound of formula-10, b) reacting the compound of formula-10 in-situ with methane sulfonic acid in presence of a suitable base in a suitable solvent to provide (2S,3R,4S,5S,6R)-2-(3-((5-(4-fluorophenyl) thiophen-2-yl)methyl)-4-methylphenyl)-6-(hydroxymethyl)tetrahydro-2H-pyran-2,3,4,5-tetraol compound of formula-5.

Wherein, in step-b) the suitable base is selected from organic (or) inorganic base;

in step-a) & b) the suitable solvent is selected from alcohol solvents, ether solvents, chloro solvents, ketone solvents, ester solvents, hydrocarbon solvents, polar aprotic solvents, polar solvents like water or mixture thereof.

The preferred embodiment of the present invention provides a process for the preparation of (2S,3R,4S,5S,6R)-2-(3-((5-(4-fluorophenyl)thiophen-2-yl)methyl)-4-methyl phenyl)-6-(hydroxymethyl) tetrahydro-2H-pyran-2,3,4,5-tetraol compound of formula-5, comprising of the following steps:

a) Reacting the 2-(4-fluorophenyl)-5-(5-iodo-2-methylbenzyl)thiophene compound of formula-4 with (3R,4S,5R,6R)-3,4,5-tris(trimethylsilyloxy)-6-((trimethylsilyloxy) methyl)tetrahydro-2H-pyran-2-one compound of formula-3 in presence of methyl lithium in tetrahydrofuran to provide (2S,3R,4S,5R,6R)-2-(3-((5-(4-fluorophenyl) thiophen-2-yl)methyl)-4-methylphenyl)-3,4,5-tris(trimethylsilyloxy)-6-((trimethyl silyloxy)methyl) tetrahydro-2H-pyran-2-ol compound of formula-10, b) reacting the compound of formula-10 in-situ with methane sulfonic acid in presence of sodium bicarbonate in methanol to provide (2S,3R,4S,5S,6R)-2-(3-((5-(4-fluoro phenyl)thiophen-2-yl)methyl)-4-methylphenyl)-6-(hydroxymethyl)tetrahydro-2H-pyran-2,3,4,5-tetraol compound of formula-5.

The fifth aspect of the present invention provides novel (2S,3R,4S,5S,6R)-2-(3-((5-(4-fluorophenyl)thiophen-2-yl) methyl)-4-methylphenyl)-6-(hydroxymethyl)tetrahydro-2H-pyran-2,3,4,5-tetraol compound of formula-5.

Formula-5

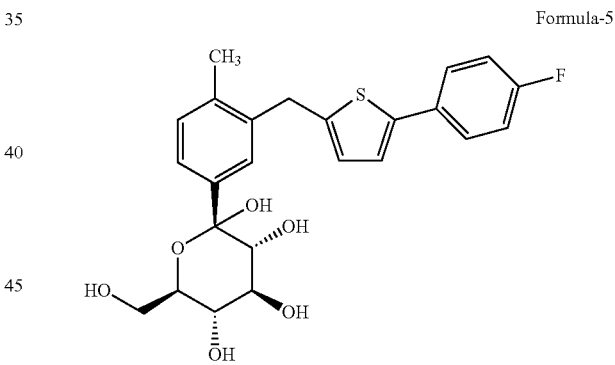

The compound of formula-5 is useful in the preparation of pure (1S)-1,5-anhydro-1-[3-[[5-(4-fluorophenyl)-2-thienyl] methyl]-4-methylphenyl]-D-glucitol compound of formula-1.

The sixth aspect of the present invention provides a process for the preparation of (1S)-1,5-anhydro-1-[3-[[5-(4-fluorophenyl)-2-thienyl]methyl]-4-methylphenyl]-D-glucitol compound of formula-1, comprising of the following steps:

a) Acetylating (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol compound of formula-5 with a suitable acetylating agent in presence of a suitable base in a suitable solvent to provide (2R,3R,4S,5R,6R)-6-(acetoxymethyl)-2-(3-((5-(4-fluorophenyl) thiophen-2-yl)methyl)-4-methylphenyl)tetrahydro-2H-pyran-2,3,4,5-tetrayltetraacetate compound of formula-11, b) reacting the compound of formula-11 with a suitable base in a suitable solvent to provide (2S,3R,4S,5S,6R)-2-(3-((5-(4-fluorophenyl)thiophen-2-yl)methyl)-4-methyl phenyl)-6-(hydroxymethyl) tetrahydro-2H-pyran-2,3,4,5-tetraol compound of formula-5, c) reducing the compound of formula-5 with a suitable reducing agent in a suitable solvent to provide pure (1S)-1,5-anhydro-1-[3-[[5-(4-fluorophenyl)-2-thienyl]methyl]-4-methyl phenyl]-D-glucitol compound of formula-1.

Wherein, in step-a) the suitable acetylating agent is same as defined in step-f) of the third aspect of the present invention;

in step-a) & b) the suitable base is selected from organic or inorganic base;

in step-c) the suitable reducing agent is same as defined in step-e) of the third aspect of the present invention;

in step-a), b) & c) the suitable solvent is selected from alcohol solvents, ether solvents, chloro solvents, ketone solvents, ester solvents, hydrocarbon solvents, polar aprotic solvents, polar solvents like water or mixture thereof.

The seventh aspect of the present invention provides novel (2R,3R,4S,5R,6R)-6-(acetoxymethyl)-2-(3-((5-(4-fluorophenyl)thiophen-2-yl)methyl)-4-methylphenyl) tetrahydro-2H-pyran-2,3,4,5-tetrayltetraacetate compound of formula-11.

Formula-11

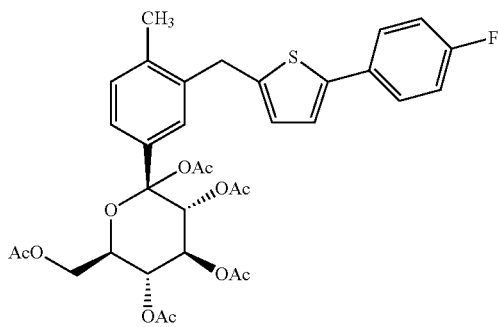

The compound of formula-11 is useful in the preparation of pure (1S)-1,5-anhydro-1-[3-[[5-(4-fluorophenyl)-2-thienyl]methyl]-4-methylphenyl]-D-glucitol compound of formula-1.

The eighth aspect of the present invention provides a process for the preparation of (1S)-1,5-anhydro-1-[3-[[5-(4-fluorophenyl)-2-thienyl]methyl]-4-methylphenyl]-D-glucitol compound of formula-1, comprising of reducing (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol compound of formula-5 with a suitable reducing agent in a suitable solvent to provide compound of formula-1.

The ninth aspect of the present invention provides a crystalline form of (2S,3R,4S,5S,6R)-2-(3-((5-(4-fluorophenyl)thiophen-2-yl)methyl)-4-methylphenyl)-6-(hydroxylmethyl)tetrahydro-2H-pyran-2,3,4,5-tetraol compound of formula-5.

The tenth aspect of the present invention provides a process for the preparation of amorphous (1S)-1,5-anhydro-1-[3-[[5-(4-fluorophenyl)-2-thienyl]methyl]-4-methylphenyl]-D-glucitol compound of formula-1, comprising of the following steps:

a) Adding (1S)-1,5-anhydro-1-[3-[[5-(4-fluorophenyl)-2-thienyl]methyl]-4-methyl phenyl]-D-glucitol compound of formula-1 to a suitable solvent, b) heating the reaction mixture, c) stirring the reaction mixture, d) cooling the reaction mixture, e) adding a suitable anti-solvent to the reaction mixture, f) filtering the precipitated solid to get amorphous (1S)-1,5-anhydro-1-[3-[[5-(4-fluorophenyl)-2-thienyl]methyl]-4-methylphenyl]-D-glucitol compound of formula-1.

Wherein, in step-a) the suitable solvent is selected from alcohol solvent, ketone solvent, ester solvent, chloro solvent, polar aprotic solvent, ether solvent and polar solvent like water or mixture thereof;

in step-b) the suitable temperature is ranging from 0° C. to the reflux temperature of solvent used in the reaction;

in step-d) the suitable temperature is ranging from −70° C. to 30° C.;

In step-e) the suitable anti-solvent is hydrocarbon solvent such as toluene, hexane, cyclohexane, n-heptane, cycloheptane, o-xylene, m-xylene, or p-xylene, pet ether, pentane, methylcyclohexane or mixture thereof.

The preferred embodiment of the present invention provides a process for the preparation of amorphous (1S)-1,5-anhydro-1-[3-[[5-(4-fluorophenyl)-2-thienyl]methyl]-4-methylphenyl]-D-glucitol compound of formula-1, comprising of the following steps:

a) Adding (1S)-1,5-anhydro-1-[3-[[5-(4-fluorophenyl)-2-thienyl]methyl]-4-methyl phenyl]-D-glucitol compound of formula-1 to dichloromethane, b) heating the reaction mixture to 40-45° C., c) stirring the reaction mixture, d) cooling the reaction mixture to −30° C. to −25, e) adding n-heptane to the reaction mixture, f) filtering the precipitated solid to get amorphous (1S)-1,5-anhydro-1-[3-[[5-(4-fluorophenyl)-2-thienyl]methyl]-4-methylphenyl]-D-glucitol compound of formula-1.

Figure 3:
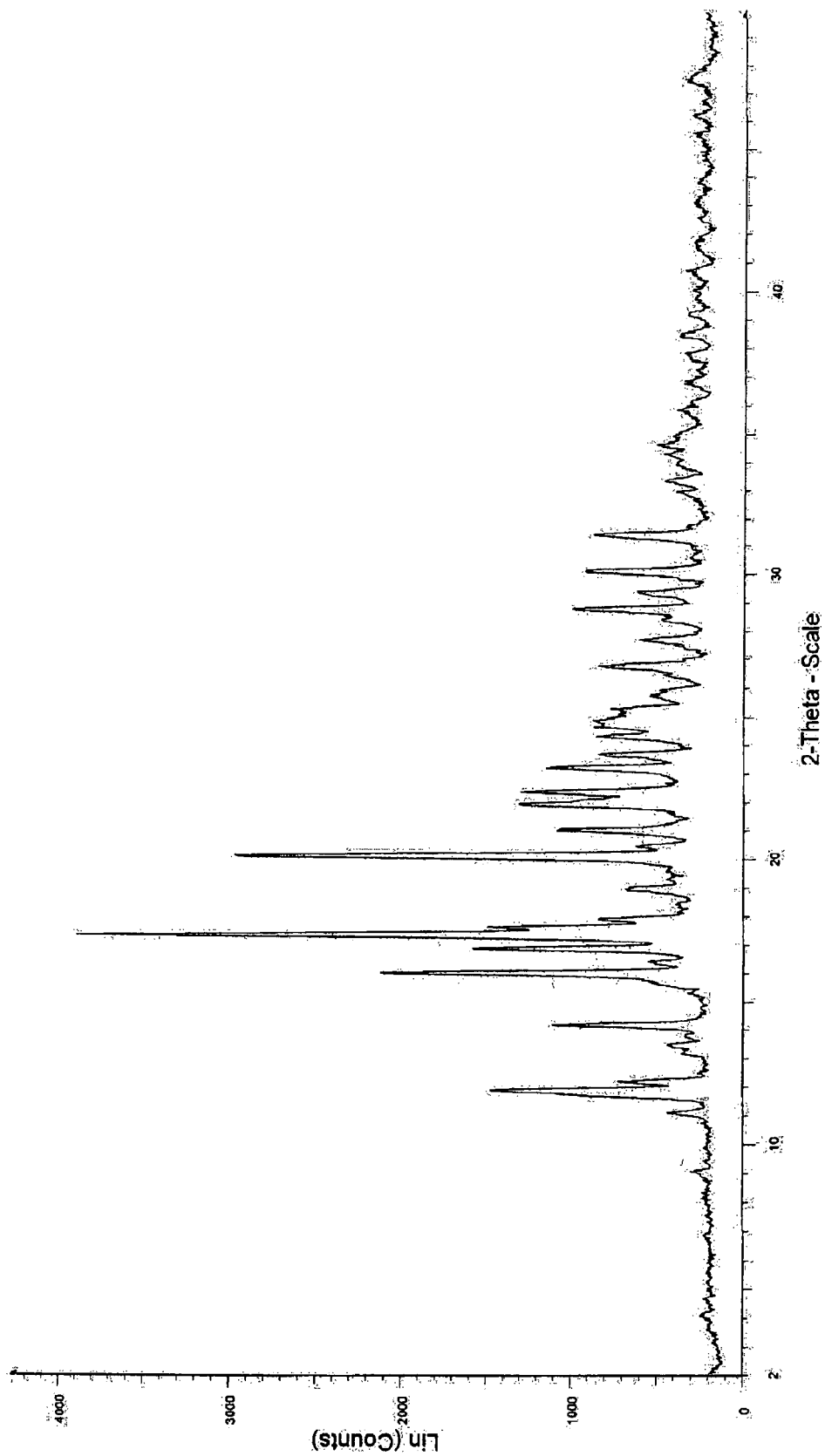
FIG. 3: Illustrates the PXRD pattern of crystalline form-M of (1S)-1,5-anhydro-1-[3-[[5-(4-fluorophenyl)-2-thienyl]methyl]-4-methylphenyl]-D-glucitol compound of formula-1.

The eleventh aspect of the present invention provides a novel crystalline from-M of (1S)-1,5-anhydro-1-[3-[[5-(4-fluorophenyl)-2-thienyl]methyl]-4-methylphenyl]-D-glucitol compound of formula-1, characterized by its powder X-ray diffractogram having peaks at 9.0, 11.0, 11.8, 12.1, 14.1, 15.9, 16.8, 17.3, 18.9, 20.0, 20.9, 21.9, 22.3, 23.2, 23.6, 24.3, 24.7, 25.2, 26.7, 27.6, 28.7, 29.3, 30.0 and 31.3±0.2 degrees of two-theta and P-XRD pattern as depicted in FIG. 3.

In an another embodiment, the said crystalline form-M is further characterized by its powder X-ray diffractogram having peaks at 4.0, 13.1, 13.4, 13.7, 15.2, 15.5, 16.3, 17.6, 19.5, 20.4, 25.7, 26.4, 28.4, 32.9, 33.3, 33.9, 34.3, 34.6, 34.9, 35.8, 37.8, 38.4, 40.7 and 47.5±0.2 degrees of two-theta.

The twelfth aspect of the present invention provides a process for the preparation of crystalline from-M (1S)-1,5-anhydro-1-[3-[[5-(4-fluorophenyl)-2-thienyl]methyl]-4-methyl phenyl]-D-glucitol compound of formula-1, comprising of the following steps:

a) Adding a suitable solvent to (1S)-1,5-anhydro-1-[3-[[5-(4-fluorophenyl)-2-thienyl] methyl]-4-methylphenyl]-D-glucitol, b) stirring the reaction mixture at a suitable temperature, c) adding the reaction mixture obtained in step-(b) to a suitable solvent, d) stirring the reaction mixture, e) filtering the precipitated solid and drying to provide crystalline form-M of (1S)-1,5-anhydro-1-[3-[[5-(4-fluorophenyl)-2-thienyl]methyl]-4-methylphenyl]-D-glucitol compound of formula-1.

Wherein, in step-a) the suitable solvent is selected from alcohol solvents, ketone solvents and polar solvent like water or mixture thereof;

in step-b) the suitable temperature is ranging from ambient temperature to reflux temperature of the solvent used in the reaction;

in step-c) the suitable solvent is selected from hydrocarbon solvents such as toluene, xylene, n-heptane, n-hexane, cyclohexane, n-pentane, pet-ether and cycloheptane or mixture thereof.

The preferred embodiment of the present invention provides a process for the preparation of crystalline form-M of (1S)-1,5-anhydro-1-[3-[[5-(4-fluorophenyl)-2-thienyl]methyl]-4-methyl phenyl]-D-glucitol compound of formula-1, comprising of the following steps:
 a) Adding acetone to (1S)-1,5-anhydro-1-[3-[[5-(4-fluorophenyl)-2-thienyl]methyl]-4-methyl phenyl]-D-glucitol,
 b) stirring the reaction mixture at 25-30° C.,
 c) adding the reaction mixture obtained in step-(b) to n-heptane,
 d) stirring the reaction mixture,
 e) filtering the precipitated solid and drying to provide crystalline form-M of (1S)-1,5-anhydro-1-[3-[[5-(4-fluorophenyl)-2-thienyl]methyl]-4-methylphenyl]-D-glucitol compound of formula-1.

The present invention also encompasses pharmaceutical compositions comprising the novel crystalline form-M of (1S)-1,5-anhydro-1-[3-[[5-(4-fluorophenyl)-2-thienyl]methyl]-4-methylphenyl]-D-glucitol compound of formula-1.

Novel crystalline form of (1S)-1,5-anhydro-1-[3-[[5-(4-fluorophenyl)-2-thienyl] methyl]-4-methylphenyl]-D-glucitol produced according to the above aspect can be prepared by using the amorphous or crystalline forms of (1S)-1,5-anhydro-1-[3-[[5-(4-fluorophenyl)-2-thienyl]methyl]-4-methylphenyl]-D-glucitol obtained from the present invention (or) processes known in the art.

The thirteenth aspect of the present invention provides amorphous solid dispersion of (1S)-1,5-anhydro-1-[3-[[5-(4-fluorophenyl)-2-thienyl]methyl]-4-methylphenyl]-D-glucitol compound of formula-1 in combination with one or more pharmaceutical acceptable carrier.

Further, the preferred embodiment of the present invention relates to amorphous solid dispersion of (1S)-1,5-anhydro-1-[3-[[5-(4-fluorophenyl)-2-thienyl]methyl]-4-methylphenyl]-D-glucitol compound of formula-1 as depicted in FIG. 1.

The fourteenth aspect of the present invention provides a process for the preparation of amorphous solid dispersion of (1S)-1,5-anhydro-1-[3-[[5-(4-fluorophenyl)-2-thienyl]methyl]-4-methylphenyl]-D-glucitol compound of formula-1 in combination with one or more pharmaceutical acceptable carrier, comprising of the following steps:
 a) Adding a suitable solvent to (1S)-1,5-anhydro-1-[3-[[5-(4-fluorophenyl)-2-thienyl] methyl]-4-methylphenyl]-D-glucitol,
 b) heating the reaction mixture to a suitable temperature,
 c) adding a suitable solvent and pharmaceutical acceptable carrier to the reaction mixture,
 d) stirring the reaction mixture,
 e) isolating amorphous solid dispersion of (1S)-1,5-anhydro-1-[3-[[5-(4-fluorophenyl)-2-thienyl]methyl]-4-methylphenyl]-D-glucitol compound of formula-1.

Wherein, in step-a) and (c) the suitable solvent is selected from alcohol solvents, chloro solvents, ester solvents, polar aprotic solvents, ketone solvents, hydrocarbon solvents and polar solvent like water or mixture thereof;

in step-b) the suitable temperature is ranging from ambient temperature to reflux temperature of the solvent used in the reaction;

in step-c) the suitable pharmaceutical acceptable carrier is selected from as defined above.

In the present invention, the composition of the solid dispersion containing of a mole ratio of the amount of the canagliflozin compound of formula-1 to the amount of the pharmaceutical acceptable carrier is ranging from about 1:0.5 to 1:10 by weight.

The preferred embodiment of the present invention provides a process for the preparation of amorphous solid dispersion of (1S)-1,5-anhydro-1-[3-[[5-(4-fluorophenyl)-2-thienyl]methyl]-4-methylphenyl]-D-glucitol compound of formula-1 in combination with HPC; comprising of the following steps:
 a) Adding methanol to (1S)-1,5-anhydro-1-[3-[[5-(4-fluorophenyl)-2-thienyl]methyl]-4-methyl phenyl]-D-glucitol,
 b) heating the reaction mixture to 40-45° C.,
 c) adding methanol and hydroxypropyl cellulose (HPC) to the reaction mixture,
 d) stifling the reaction mixture,
 e) isolating amorphous solid dispersion of (1S)-1,5-anhydro-1-[3-[[5-(4-fluorophenyl)-2-thienyl]methyl]-4-methylphenyl]-D-glucitol compound of formula-1 in combination with HPC.

Another, preferred embodiment of the present invention provides a process for the preparation of amorphous solid dispersion of (1S)-1,5-anhydro-1-[3-[[5-(4-fluorophenyl)-2-thienyl] methyl]-4-methylphenyl]-D-glucitol compound of formula-1 in combination with HPC; comprising of the following steps:
 a) Adding dichloromethane to (1S)-1,5-anhydro-1-[3-[[5-(4-fluorophenyl)-2-thienyl] methyl]-4-methyl phenyl]-D-glucitol,
 b) heating the reaction mixture to 40-45° C.,
 c) adding dichlormethane and hydroxypropyl cellulose (HPC) to the reaction mixture,
 d) stirring the reaction mixture,
 e) isolating amorphous solid dispersion of (1S)-1,5-anhydro-1-[3-[[5-(4-fluorophenyl)-2-thienyl] methyl]-4-methylphenyl]-D-glucitol compound of formula-1 in combination with HPC.

The amorphous solid dispersion of (1 S)-1,5-anhydro-1-[3-[[5-(4-fluorophenyl)-2-thienyl] methyl]-4-methylphenyl]-D-glucitol obtained according to the present invention can be isolated using a rotational distillation device such as a Buchi Rotavapor, vacuum drying, spray drying, spray granulating, freeze drying and spray-freeze drying, agitated thin film drying (ATFD) or melt extrusion or freeze drying (lyophilization) or by any other suitable techniques.

The amorphous solid dispersion of (1S)-1,5-anhydro-1-[3-[[5-(4-fluorophenyl)-2-thienyl]methyl]-4-methyl phenyl]-D-glucitol obtained according to the present invention can be prepared from the crystalline (or) amorphous forms of (1S)-1,5-anhydro-1-[3-[[5-(4-fluorophenyl)-2-thienyl]methyl]-4-methylphenyl]-D-glucitol obtained from the present invention (or) processes known in the art.

Preferred solid dispersions are "solid solutions", where the dispersion of the components is such that the system is chemically and physically uniform or homogeneous throughout or even consists of one phase as defined by measurement of thermodynamic properties of the system, e.g. the amorphous canagliflozin and the water soluble excipients form a system that is chemically and physically uniform or homogeneous throughout or even consists of one phase as defined by measurement of thermodynamic properties of the system.

The invention also encompasses pharmaceutical compositions comprising the amorphous solid dispersion of (1S)-1,5-anhydro-1-[3-[[5-(4-fluorophenyl)-2-thienyl]methyl]-4-methyl phenyl]-D-glucitol of the invention. As used herein, the term "pharmaceutical compositions" or "pharmaceutical formulations" include tablets, pills, powders, liquids, suspensions, emulsions, granules, capsules, suppositories, or injection preparations.

Pharmaceutical compositions containing the amorphous solid dispersion of (1S)-1,5-anhydro-1-[3-[[5-(4-fluorophenyl)-2-thienyl]methyl]-4-methylphenyl]-D-glucitol of the invention may be prepared by using diluents or excipients such as fillers, bulking agents, binders, wetting agents, disintegrating agents, coloring agents, flavoring agents, stabilizers, lubricants/glidants, plasticizers and surface active agents. Various modes of administration of the pharmaceutical compositions of the invention can be selected depending on the therapeutic purpose, for example tablets, pills, powders, liquids, suspensions, emulsions, granules, capsules, suppositories, or injection preparations.

The invention also encompasses pharmaceutical compositions comprising (1S)-1,5-anhydro-1-[3-[[5-(4-fluorophenyl)-2-thienyl]methyl]-4-methylphenyl]-D-glucitol of the present invention. As used herein, the term "pharmaceutical compositions" or "pharmaceutical formulations" include tablets, pills, powders, liquids, suspensions, emulsions, granules, capsules, suppositories, or injection preparations.

The amorphous solid dispersion of canagliflozin compound of formula-1 of the present invention may optionally be micronized to obtain the micronized amorphous solid dispersion of canagliflozin by the conventional methods known in the art.

Amorphous (1S)-1,5-anhydro-1-[3-[[5-(4-fluorophenyl)-2-thienyl]methyl]-4-methyl phenyl]-D-glucitol compound of formula-1 produced by the present invention containing less than about 0.1% area by HPLC of one or more of the following impurities:

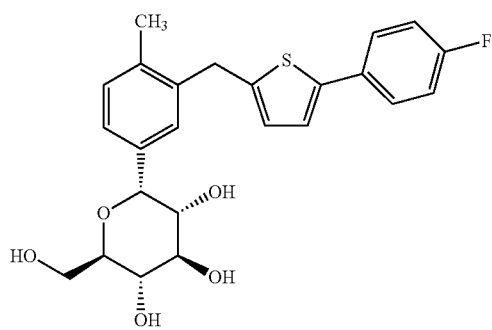

(2R,3R,4R,5S,6R)-2-(3-((5-(4-Fluorophenyl)
thiophen-2-yl)methyl)-4-methyl phenyl)-6-
(hydroxymethyl)tetrahydro-2H-pyran-3,4,5-
triol [Alpha Isomer]

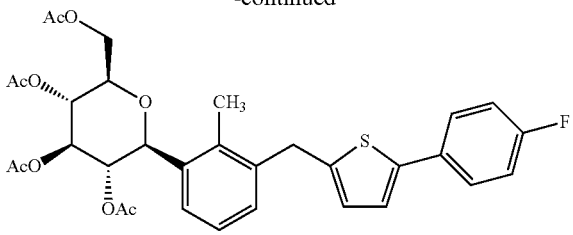

(2R,3R,4R,5S,6S)-2-(Acetoxymethyl)-6-(3-((5-
(4-fluorophenyl)thiophen-2-yl)methyl)-2-
methylphenyl)tetrahydro-2H-pyran-3,4,5-triyl
triacetate [3-Acetyl Impurity]

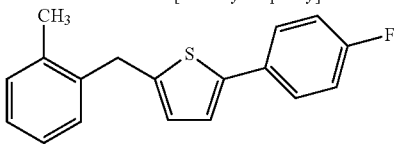

2-(4-Fluorophenyl)-5-(2-methylbenzyl)
thiophene [Methyl Impurity]

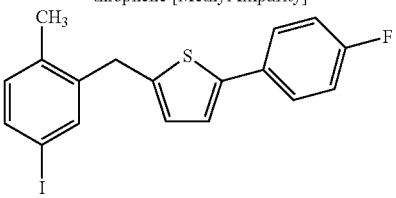

2-(4-Fluorophenyl)-5-(5-iodo-2-methylbenzyl)
thiophene [Iodo Impurity]

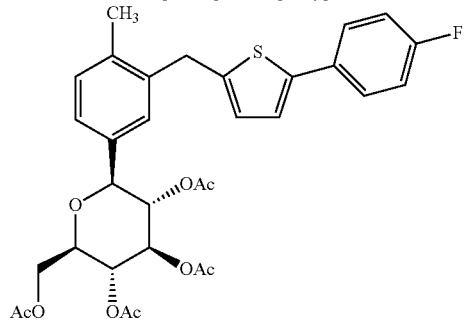

(2R,3R,4R,5S,6S)-2-(Acetoxymethyl)-6-(3-((5-
(4-fluorophenyl)thiophen-2-yl)methyl)-4-
methylphenyl)tetrahydro-2H-pyran-3,4,5-triyl
triacetate [Acetyl Impurity]

Amorphous (1 S)-1,5-anhydro-1-[3-[[5-(4-fluorophenyl)-2-thienyl]methyl]-4-methyl phenyl]-D-glucitol compound of formula-1 produced by the present invention can be further micronized or milled in a conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

(1S)-1,5-anhydro-1-[3-[[5-(4-fluorophenyl)-2-thienyl]methyl]-4-methylphenyl]-D-glucitol compound of formula-1 produced by the present invention can be further micronized or milled by the conventional techniques to get the desired particle size to achieve desired solubility profile based on different forms of pharmaceutical composition requirements.

P-XRD Method of Analysis:
PXRD analysis of compound of formula-1 produced by the present invention were carried out using BRUKER/AXS X-Ray diffractometer using Cu Kα radiation of wavelength 1.5406 A° and continuous scan speed of 0.03°/min.

DSC Method of Analysis:

Differential scanning calorimetric (DSC) analysis was performed with Q10 V9.6 Build 290 calorimeter. Samples of about 2 to 3 milligrams held in a closed pan were analyzed at a heating rate of 10° per minute.

HPLC Method of Analysis of Amorphous (1S)-1,5-anhydro-1-[3-[[5-(4-fluorophenyl)-2-thienyl]methyl]-4-methyl phenyl]-D-glucitol Compound of Formula 1

Apparatus: A liquid chromatographic system is to be equipped with variable wavelength UV-detector; Column: Unison UK-C18, 150×4.6 mm, 3 μm (or) equivalent; Flow rate: 1.0 ml/min; Wavelength: 290 nm; Column Temperature: 35° C.; Injection volume: 10 μL; Run time: 40 min; Auto sampler temperature: 5° C.; Diluent: Acetonitrile:Water (90:10 v/v); Needle wash: Methanol; Elution: Gradient; Mobile phase-A: Buffer (100%); Mobile phase-B: Acetonitrile:Water (90:10 v/v); Buffer: Transfer 1.0 ml of Orthophosphoric acid (85%) into 1000 ml of Milli-Q-water, mix well and filter this solution through 0.22 μm Nylon membrane filter paper.

The process of the present invention can be represented schematically as follows:

Scheme-I

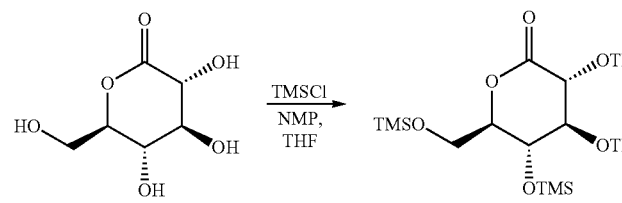
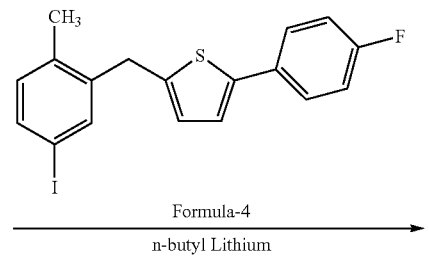

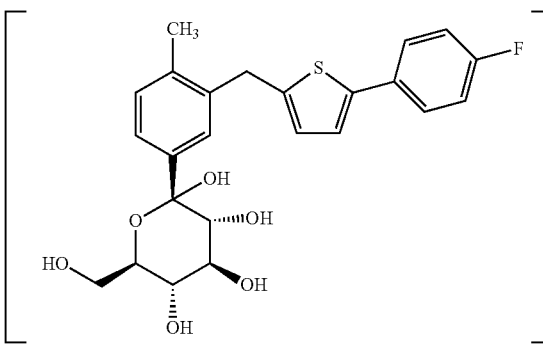

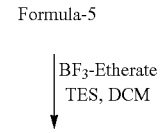

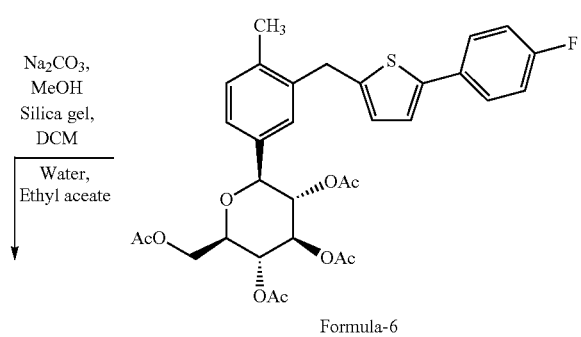
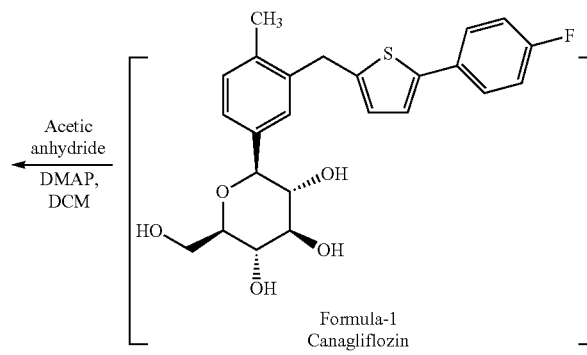

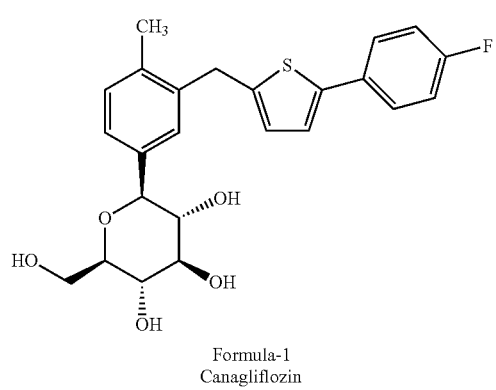
Formula-1
Canagliflozin
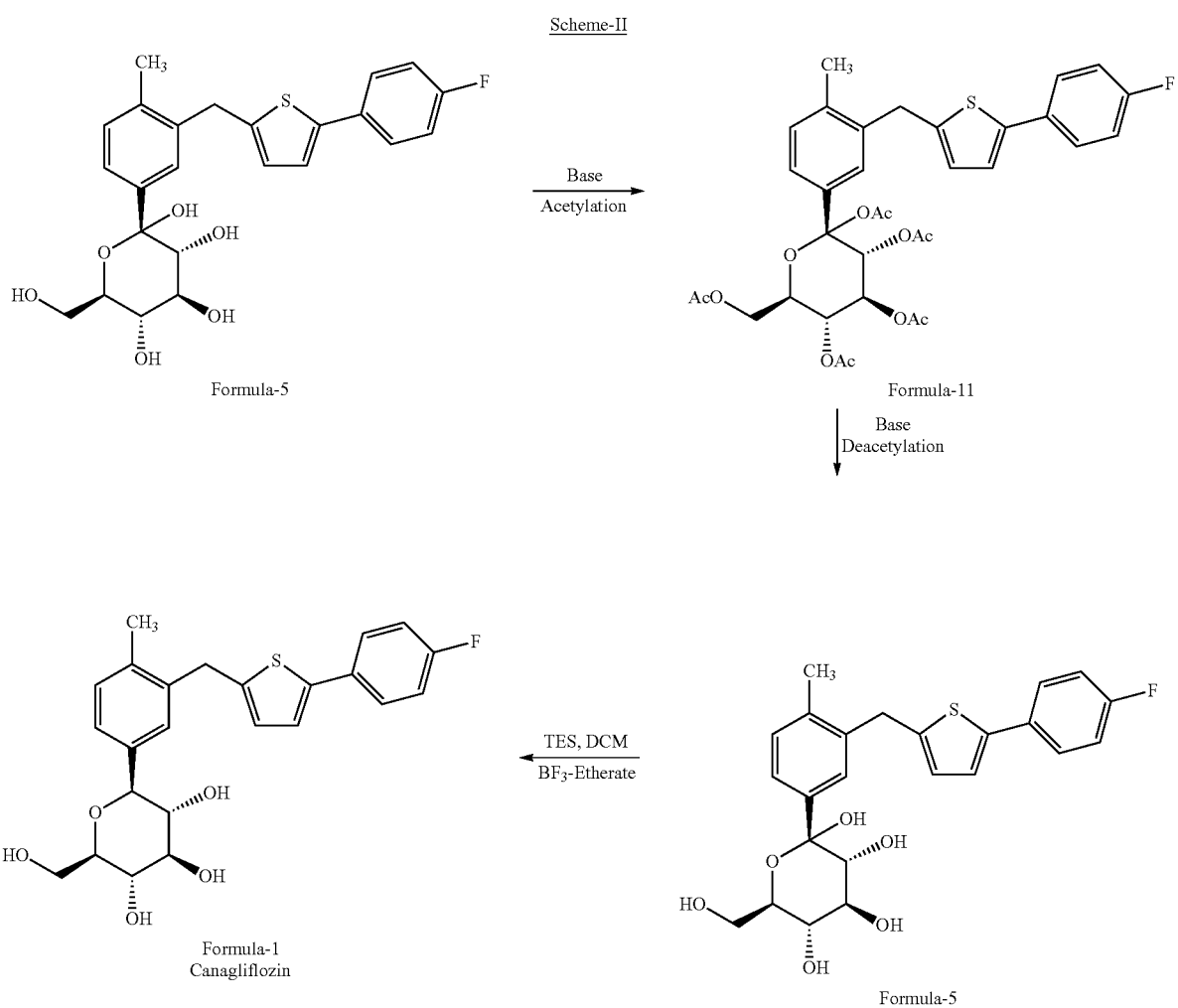 [SMILES: Cc1ccc([C@]2(O)O[C@H](CO)[C@@H](O)[C@H](O)[C@H]2O)cc1Cc1ccc(-c2ccc(F)cc2)s1 ; CC(=O)OC[C@H]1O[C@@](OC(C)=O)(c2ccc(C)c(Cc3ccc(-c4ccc(F)cc4)s3)c2)[C@H](OC(C)=O)[C@@H](OC(C)=O)[C@@H]1OC(C)=O ; Cc1ccc([C@@H]2O[C@H](CO)[C@@H](O)[C@H](O)[C@H]2O)cc1Cc1ccc(-c2ccc(F)cc2)s1 ; Cc1ccc([C@]2(O)O[C@H](CO)[C@@H](O)[C@H](O)[C@H]2O)cc1Cc1ccc(-c2ccc(F)cc2)s1]
The process described in the present invention was demonstrated in examples illustrated below. These examples are provided as illustration only and therefore should not be construed as limitation of the scope of the invention.

EXAMPLES

Example-1: One-Pot Process for the Preparation of (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyl triacetate (Formula-6)

a) Preparation of (3R,4S,5R,6R)-3,4,5-tris(trimethylsilyloxy)-6-((trimethylsilyloxy) methyl)tetrahydro-2H-pyran-2-one (Formula-3)

A mixture of tetrahydrofuran (200 ml), (3R,4S,5S,6R)-3,4,5-trihydroxy-6-(hydroxyl methyl)tetrahydro-2H-pyran-2-one (20 gms) compound of formula-2 and N-methyl morpholine (102.96 gms) was cooled to 0-5° C. and stirred for 20 minutes at the same temperature. Trimethyl silyl chloride (91.2 gms) was slowly added to the reaction mixture at 0-5° C. Raised the temperature of the reaction mixture to 40-45° C. and stirred for 5 hours at the same temperature. Cooled the reaction mixture to 25-30° C. and stirred for 12 hours at the same temperature. Further, cooled the reaction mixture to 0-5° C. n-heptane (100 ml), followed by water (100 ml) was slowly added to the reaction mixture at 0-5° C. Raised the temperature of the reaction mixture 25-30° C. Both the organic and aqueous layers were separated and the aqueous layer was extracted with n-heptane. Combined the organic layers and washed with aqueous disodium hydrogen phosphate solution and followed by aqueous sodium chloride solution. Dried the organic layer with sodium sulfate. Distilled off the solvent completely from the organic layer under reduced pressure to get the title compound.

b) Preparation of (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol (Formula-5)

2-(4-Fluorophenyl)-5-(5-iodo-2-methylbenzyl)thiophene (25 gms) compound of formula-4 and tetrahydrofuran (175 ml) were added to the compound of formula-3 obtained in above step-a) at 25-30° C. under nitrogen atmosphere. Cooled the reaction mixture to −75 to −70° C. n-butyl lithium (71 ml) was added to the reaction mixture at −75 to −70° C. and stirred for 1 hour at the same temperature under nitrogen atmosphere. Methanol (10 ml) was slowly added to the reaction mixture at −75 to −70° C. and stirred for 1 hour at the same temperature. Aqueous sodium bicarbonate solution (5 gms of sodium carbonate in 50 ml of water) was slowly added to the reaction mixture at −75° C. to −70° C. under nitrogen atmosphere. Raised the temperature of the reaction mixture to 25-30° C. Water (250 ml) was added to the reaction mixture at 25-30° C. and stirred for 30 minutes at the same temperature. Both the organic and aqueous layers were separated and the aqueous layer was extracted with ethyl acetate. Combined the organic layers and washed with aqueous sodium chloride solution. Dried the organic layer with sodium sulfate. Distilled off the solvent completely under reduced pressure to get the title compound.

c) Preparation of (1S)-1,5-anhydro-1-[3-[[5-(4-fluorophenyl)-2-thienyl]methyl]-4-methylphenyl]-D-glucitol (Formula-1)

Dichloromethane (175 ml) was added to the compound of formula-5 obtained in the above step-b) at 25-30° C. and stirred for 10 minutes at the same temperature. Cooled the reaction mixture to −25° C. −20° C. Triethyl silane (24.02 gms) was slowly added to the above pre-cooled reaction mixture at −25° C. to −20° C. and stirred for 45 minutes at the same temperature. $BF_3$-etherate (27.6 gms) was slowly added to the reaction mixture at −25° C. to −20° C. Raised the temperature of the reaction mixture to 25-30° C. and stirred for 2 hours at the same temperature. Ethyl acetate followed by water was slowly added to the reaction mixture at 25-30° C. and stirred for 15 minutes at the same temperature. Both the organic and aqueous layers were separated and aqueous layer was extracted with ethyl acetate. Combined the organic layers and the aqueous sodium bicarbonate solution was added to the organic layer. Adjusted the pH of the reaction mixture to 7-8 using acetic acid. Separated the organic and aqueous layers and washed the organic layer using aqueous sodium bicarbonate solution and then followed by aqueous sodium chloride solution. Dried the organic layer using sodium sulfate. Distilled off the organic layer completely under reduced pressure to get the title compound.

d) Preparation of (2R,3R,4R,5S,6S)-2-(acetoxymethyl)-6-(3-((5-(4-fluorophenyl) thiophen-2-yl) methyl)-4-methylphenyl)tetrahydro-2H-pyran-3,4,5-triyltriacetate (Formula-6)

Dichloromethane (175 ml) was added to the compound of formula-1 obtained in the above step-c) at 25-30° C. and stirred for 10 minutes. Dimethyl aminopyridine (1.73 gms) followed by acetic anhydride (36.14 gms) was slowly added to the reaction mixture at 25-30° C. and stirred the reaction mixture for 3 hours at the same temperature. Water was added to the reaction mixture at 25-30° C. Both the organic and aqueous layers were separated and aqueous layer was extracted with dichloromethane. Combined the organic layers and washed with aqueous hydrochloric acid solution. Organic layer was washed with aqueous sodium bicarbonate solution and followed by sodium chloride solution. Distilled off the solvent completely from the organic layer and then co-distilled with methanol. To the obtained compound, methanol (75 ml) was added at below 50° C. Cooled the reaction mixture to 25-30° C. and stirred for 2 hours at the same temperature. Filtered the precipitated solid, washed with methanol and dried to get the title compound.

Yield: 19.23 gms.

Example-2: Preparation of Amorphous (1S)-1,5-anhydro-1-[3-[[5-(4-fluorophenyl)-2-thienyl]methyl]-4-methylphenyl]-D-glucitol (Formula-1)

A mixture of methanol (225 ml), (2R,3R,4R,5S,6S)-2-(acetoxymethyl)-6-(3-((5-(4-fluoro phenyl)thiophen-2-yl)methyl)-4-methylphenyl)tetrahydro-2H-pyran-3,4,5-triyltriacetate (25 gms), sodium carbonate (75 gms) and water (25 ml) were heated to 60-65° C. and stirred for 20 hours at the same temperature. Cooled the reaction mixture to 25-30° C. Filtered the reaction mixture and washed with methanol. Distilled off the solvent completely from the filtrate under reduced pressure. Dichloromethane (175 ml) and silica gel (50 gms) were added to the obtained compound at 25-30° C. Distilled off the solvent completely from the reaction mixture under reduced pressure. Methanol (100 ml) was added to the obtained compound at 25-30° C. and stirred 15 minutes at the same temperature. Water (200 ml) was slowly added to the reaction mixture at 25-30° C. and stirred for 45 minutes at the same temperature. Filtered the reaction mixture and washed with water. To the obtained wet compound, dichloromethane (175 ml) was added at 25-30° C. Heated the reaction mixture to 40-45° C. and stirred for 20 minutes at the same temperature. Filtered the reaction mixture through hy-flow bed and washed with dichloromethane. To the obtained filtrate, ethyl acetate (25 ml) and carbon (2.5 gms) were added at 25-30° C. Filtered the reaction mixture and distilled off the solvent completely from the filtrate under reduced pressure to get the title compound.

Yield: 12.9 gms; M.R: 60-70° C.; Purity by HPLC: 99.93%;

Alpha isomer: 0.01%; 2-methyl phenyl impurity: N/D; Acetyl impurity: N/D; Methyl impurity: N/D; Iodo impurity: N/D; HIUI: 0.06%.

Particle size distribution: D(0.9): 14.5 μm; D(0.5): 7.69 μm; D(0.1): 3.29 μm.

The P-XRD pattern of the obtained compound was depicted in FIG. 1.

Example-3: Preparation of Amorphous (1S)-1,5-anhydro-1-[3-[[5-(4-fluorophenyl)-2-thienyl] methyl]-4-methylphenyl]-D-glucitol (Formula-1)

A mixture of methanol (225 ml), (2R,3R,4R,5S,6S)-2-(acetoxymethyl)-6-(3-((5-(4-fluoro phenyl)thiophen-2-yl) methyl)-4-methylphenyl)tetrahydro-2H-pyran-3,4,5-triyltriacetate (25 gms), sodium carbonate (75 gms) and water (25 ml) was heated to 60-65° C. and stirred for 20 hours at the same temperature. Cooled the reaction mixture to 25-30° C. Filtered the reaction mixture and washed with methanol. Distilled off the solvent completely from the filtrate under reduced pressure. Dichloromethane (175 ml) and silica gel (50 gms) were added to the obtained compound at 25-30° C. Distilled off the solvent completely from the reaction mixture under reduced pressure. Methanol (100 ml) and water (200 ml) was added to the obtained compound at 25-30° C. and stirred 45 minutes at the same temperature. Filtered the solid from the reaction mixture. To the obtained compound, dichloromethane (175 ml) was added at 25-30° C. Heated the reaction mixture to 40-45° C. and stirred for 20 minutes at the same temperature. Filtered the reaction mixture through hy-flow bed and washed with dichloromethane. To the obtained filtrate, ethyl acetate (25 ml) and carbon (2.5 gms) were added at 25-30° C. Filtered the reaction mixture through hy-flow bed and distilled off the solvent completely from the filtrate under reduced pressure to get the title compound. Yield: 12.4 gms.

The P-XRD pattern of the obtained compound was depicted in FIG. 1.

Example-4: Preparation of Amorphous (1S)-1,5-anhydro-1-[3-[[5-(4-fluorophenyl)-2-thienyl] methyl]-4-methylphenyl]-D-glucitol (Formula-1)

A mixture of dichloromethane (700 ml) and (1S)-1,5-anhydro-1-[3-[[5-(4-fluorophenyl)-2-thienyl]methyl]-4-methylphenyl]-D-glucitol (50 gms) were stirred for 30 minutes at 40-45° C. Filtered the reaction mixture and distilled off the solvent completely under reduced pressure. n-Heptane (250 ml) was added to the obtained compound and distilled off the solvent completely from the reaction mixture under reduced pressure. n-Heptane (250 ml) was added to the obtained compound at 25-30° C. and stirred for 30 minutes at the same temperature. Filtered the solid and washed with n-heptane. Dried the compound at 50-55° C. and sieve the compound with 100 mesh to get the title compound.

Yield: 42 gms; Purity by HPLC: 99.94%;

Particle size distribution: D(0.9): 116.4 μm; D(0.5): 61.4 μm; D(0.1): 28.7 μm.

Example-5: Preparation of Amorphous (1S)-1,5-anhydro-1-[3-[[5-(4-fluorophenyl)-2-thienyl] methyl]-4-methylphenyl]-D-glucitol (Formula-1)

A mixture of methanol (90 lts), (2R,3R,4R,5S,6S)-2-(acetoxymethyl)-6-(3-((5-(4-fluoro phenyl)thiophen-2-yl) methyl)-4-methylphenyl)tetrahydro-2H-pyran-3,4,5-triylacetate (10 kgs), sodium carbonate (30 kgs) and water (10 lts) was heated to 60-65° C. and stirred for 20 hours at the same temperature. Cooled the reaction mixture to 25-30° C. Filtered the reaction mixture and washed with methanol. Distilled off the solvent completely from the filtrate under reduced pressure. Dichloromethane (45 lts) and silica gel (40 kgs) were added to the obtained compound at 25-30° C. Distilled off the solvent completely from the reaction mixture under reduced pressure. Methanol (60 lts) was added to the obtained compound at 25-30° C. and stirred 15 minutes at the same temperature. Water (120 lts) was slowly added to the reaction mixture at 25-30° C. and stirred for 45 minutes at the same temperature. Filtered the solid and washed with water. To the obtained wet compound, dichloromethane (105 lts) was added at 25-30° C. Heated the reaction mixture to 40-45° C. and stirred for 20 minutes at the same temperature. Filtered the reaction mixture through hy-flow bed and washed with dichloromethane. To the obtained filtrate, ethyl acetate (10 lts) and carbon (1 kg) were added at 25-30° C. and stirred for 10 minutes at the same temperature. Filtered the reaction mixture through hy-flow bed and distilled off the solvent completely from the filtrate under reduced pressure to get the title compound.

Yield: 5 kgs.

The P-XRD pattern of the obtained compound was depicted in FIG. 1.

Example-6: Preparation of (5-(4-fluorophenyl)thiophen-2-yl)(5-iodo-2methyl)phenyl) methanone (Formula-9)

A mixture of dichloromethane (250 ml), dimethyl formamide (0.5 ml) and 5-iodo-2-methylbenzoic acid (50 gms) compound of formula-7 were cooled to 15-20° C. Thionyl chloride (31.8 gms) was slowly added to the reaction mixture at 15-20° C. and stirred for 6 hours at the same temperature. Distilled off the solvent completely under reduced pressure. Dichloromethane (110 ml) was added to the obtained compound under nitrogen atmosphere. Cooled the reaction mixture to 0-5° C. Aluminum chloride (21.61 gms) was added to the reaction mixture at 0-5° C. and stirred for 20 minutes at the same temperature. A solution of 2-(4-fluorophenyl)thiophene (34.0 gms) in dichloromethane (55 ml) was added to the reaction mixture at 0-5° C. Raised the temperature of the reaction mixture to 25-30° C. and stirred for 4 hours at the same temperature. The reaction mixture was slowly added to a pre-cooled aqueous HCl solution at 0-5° C. and stirred for 15 minutes at the same temperature. Raised the temperature of the reaction mixture to 25-30° C. Both the organic and aqueous layers were separated and the aqueous layer was extracted with dichloromethane. Combined both the organic layers and washed with aqueous sodium bicarbonate solution and dried over sodium sulfate. Distilled off the solvent completely under reduced pressure. Methanol (150 ml) was added to the obtained compound at 25-30° C. and stirred for 45 minutes at the same temperature. Filtered the solid, washed with methanol and dried to get the title compound. Yield: 60 gms; Melting point: 135.1-137.2° C.

Example-7: Preparation of 2-(4-fluorophenyl)-5-(5-iodo-2-methylbenzyl)thiophene (Formula-4)

Triethyl silane (164 gms) was added to a mixture of (5-(4-fluorophenyl)thiophen-2-yl)(5-iodo-2-methylphenyl) methanone (200 gms) and acetonitrile (500 ml) at 25-30° C. Cooled the reaction mixture to 0-5° C. BF$_3$-etherate (160 gms) was slowly added to the reaction mixture at 0-5° C. Raised the temperature of the reaction mixture to 25-30° C. and stirred for 4 hours at the same temperature. Cooled the reaction mixture to 0-5° C. and stirred for 1 hour at the same temperature. Filtered the compound and washed with acetonitrile. Water (600 nil) was added to the obtained wet compound at 25-30° C. Neutralized the reaction mixture using aqueous sodium bicarbonate solution at 25-30° C. and stirred for 1 hour at the same temperature. Filtered the solid, washed with water and dried to get the title compound. Yield: 172 gms; Melting point: 110-115° C.

Example-8: Preparation of (3R,4S,5R,6R)-3,4,5-tris (trimethylsilyloxy)-6-((trimethyl silyloxy)methyl) tetra hydro-2H-pyran-2-one (Formula-3)

A mixture of tetrahydrofuran (400 ml), (3R,4S,5S,6R)-3,4,5-trihydroxy-6-(hydroxyl methyl)tetrahydro-2H-pyran-2-one (50 gms) and N-methyl morpholine (205.92 gms) was cooled to 0-5° C. and stirred for 20 minutes at the same temperature. Trimethyl silyl chloride (182.4 gms) was slowly added to the reaction mixture at 0-5° C. Raised the temperature of the reaction mixture to 40-45° C. and stirred for 5 hours at the same temperature. Cooled the reaction mixture to 25-30° C. and stirred for 12 hours at the same temperature. Further, cooled the reaction mixture to 0-5° C. n-heptane (200 ml) followed by water (200 ml) was added to the reaction mixture at 0-5° C. Raised the temperature of the reaction mixture 25-30° C. Both the organic and aqueous layers were separated and aqueous layer was extracted with n-heptane. Combined the organic layers and washed with disodium hydrogen phosphate solution and followed by sodium chloride solution. Distilled off the solvent completely from the organic layer under reduced pressure to get the title compound.

Example-9: Preparation of (2S,3R,4S,5S,6R)-2-(3-((5-(4-fluorophenyl)thiophen-2-yl)methyl)-4-methylphenyl)-6-(hydroxymethyl)tetrahydro-2H-pyran-2,3,4,5-tetraol (Formula-5)

2-(4-Fluorophenyl)-5-(5-iodo-2-methylbenzyl)thiophene (50 gms) compound of formula-4 and tetrahydrofuran (350 ml) were added to the compound obtained in example-8 at 25-30° C. under nitrogen atmosphere. Cooled the reaction mixture to −75 to −70° C. Methyl lithium (116 ml) was added to the reaction mixture at −75 to −70° C. and stirred for 1 hour at the same temperature under nitrogen atmosphere. Methane sulfonic acid solution (11.8 gms) in 250 ml of methanol was slowly added to the reaction mixture at −75 to −70° C. Water was added to the reaction mixture at −75° C. to −70° C. under nitrogen atmosphere. Aqueous sodium bicarbonate solution (20 gms of sodium bicarbonate in 100 ml of water) was slowly added to the reaction mixture at −75° C. Raised the temperature of the reaction mixture to 25-30° C. Both the organic and aqueous layers were separated and aqueous layer was extracted with ethyl acetate. Combined the organic layers and washed with aqueous sodium chloride solution. Distilled off the solvent completely under reduced pressure to get the title compound.

Example-10: Preparation of (1S)-1,5-anhydro-1-[3-[[5-(4-fluorophenyl)-2-thienyl]methyl]-4-methylphenyl]-D-glucitol (Formula-1)

Dichloromethane (350 ml) was added to the compound obtained in example-9 at 25-30° C. Cooled the reaction mixture to −25° C. to −20° C. Triethyl silane (48.04 gms) was slowly added to the above reaction mixture at −25° C. to −20° C. and stirred for 45 minutes at the same temperature. BF$_3$-etherate (55.2 gms) was slowly added to the above reaction mixture at −25° C. to −20° C. Raised the temperature of the reaction mixture to 25-30° C. and stirred for 4 hours at the same temperature. Ethyl acetate and followed by water was added to the reaction mixture and stirred for 15 minutes at the same temperature. Both the organic and aqueous layers were separated and aqueous layer was extracted with ethyl acetate. Combined the organic layers and washed with aqueous sodium bicarbonate solution and followed by aqueous sodium chloride solution. Distilled off the solvent completely from the organic layer under reduced pressure to get the title compound.

Example-11: Preparation of (2R,3R,4R,5S,6S)-2-(acetoxymethyl)-6-(3-((5-(4-fluoro phenyl)thiophen-2-yl)methyl)-4-methylphenyl)tetrahydro-2H-pyran-3,4,5-triyl triacetate (Formula-6)

Dichloromethane (350 ml) and dimethyl aminopyridine (3.46 gms) was added to the compound obtained in example-10 at 25-30° C. Acetic anhydride (72.5 gms) was slowly added to the reaction mixture at 25-30° C. and stirred for 3 hours at the same temperature. Water was added to the reaction mixture at 25-30° C. Both the organic and aqueous layers were separated and the aqueous layer was extracted with dichloromethane. Combined the organic layers and washed with aqueous hydrochloric acid solution. Organic layer was washed with the aqueous sodium bicarbonate solution and followed by sodium chloride solution. Distilled off the solvent completely under reduced pressure and co-distilled with methanol. To the obtained compound, methanol (200 ml) was added and stirred the reaction mixture for 2 hours at 25-30° C. Filtered the solid, washed with methanol and dried to get the title compound. Yield: 21 gms.

Example-12: Purification of (2R,3R,4R,5S,6S)-2-(acetoxymethyl)-6-(3-((5-(4-fluoro phenyl)thiophen-2-yl)methyl)-4-methylphenyl)tetrahydro-2H-pyran-3,4,5-triyl triacetate (Formula-6)

Ethyl acetate (375 ml) was added to (2R,3R,4R,5S,6S)-2-(acetoxymethyl)-6-(3-((5-(4-fluorophenyl)thiophen-2-yl) methyl)-4-methylphenyl)tetrahydro-2H-pyran-3,4,5-triyl triacetate (50 gms) at 25-30° C. Heated the reaction mixture to 55-60° C. and stirred for 15 minutes at the same temperature. Carbon (5 gms) was added to the reaction mixture at 55-60° C. and stirred for 15 minutes at the same temperature. Filtered the reaction mixture through hyflow bed and washed with ethyl acetate. Distilled off the solvent completely from the filtrate under reduced pressure. Ethyl acetate (25 ml) and methanol (250 ml) were added to the obtained compound at 25-30° C. Heated the reaction mixture to 55-60° C. and stirred for 45 minutes at the same temperature. Cooled the reaction mixture to 25-30° C. and further cooled to 15-20° C. and stirred for 1 hour at the same temperature. Filtered the precipitated solid and washed with methanol. To the obtained wet compound, ethyl acetate (250 ml) was added at 25-30° C. Heated the reaction mixture to 55-60° C. and stirred the reaction mixture for 15 minutes at the same temperature. Distilled off the solvent completely from the reaction mixture under reduced pressure. Ethyl acetate (25 ml) and methanol (250 ml) was added to the obtained compound at 25-30° C. Heated the reaction mixture to 55-60° C. and stirred for 45 minutes at the same temperature. Cooled the reaction mixture to 25-30° C. Further cooled the reaction mixture to 15-20° C. and stirred for 1 hour at the same temperature. Filtered the precipitated solid, washed with methanol and dried to get the title compound. Yield: 35.5 gms.

Example-13: Preparation of (1S)-1,5-anhydro-1-[3-[[5-(4-fluorophenyl)-2-thienyl] methyl]-4-methyl phenyl]-D-glucitol (Formula-1)

Methanol (225 ml) was added to (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyl triacetate (25 gms) compound of formula-6 at 25-30° C. Sodium carbonate (75 gms) and followed by water (25 ml) was added to the reaction mixture at 25-30° C. Heated the reaction mixture to 60-65° C. and stirred for 20 hours at the same temperature. Cooled the reaction mixture to 25-30° C. Filtered the reaction mixture and washed with methanol. Distilled off the solvent about 50% from the filtrate under reduced pressure. Cooled the reaction mixture to 25-30° C. Activated carbon (2.5 gms) was added to the reaction mixture and stirred for 30 minutes at 25-30° C. Filtered the reaction mixture and washed with methanol. The reaction mixture was slowly added to water (250 ml) at 25-30° C. and stirred for 45 minutes at the same temperature. Filtered the precipitated solid, washed with water and dried to get the title compound. Yield: 17 gms; Melting point: 100-110° C.; Purity by HPLC: 99.85%.

The P-XRD pattern of the obtained compound of formula-1 is matching with the P-XRD pattern of canagliflozin hemihydrate disclosed in U.S. Pat. No. 7,943,582 B2.

Example-14: Purification of (2R,3R,4R,5S,6S)-2-(acetoxymethyl)-6-(3-((5-(4-fluoro phenyl)thiophen-2-yl)methyl)-4-methylphenyl)tetrahydro-2H-pyran-3,4,5-triyltriacetate (Formula-6)

The mixture of acetonitrile (250 ml) and (2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyl triacetate (50 gms) was heated to 80-85° C. and stirred the reaction mixture for 20 minutes at the same temperature. Cooled the reaction mixture to 10-15° C. and stirred for 1½ hour at the same temperature. Filtered the precipitated solid, washed with acetonitrile and dried to get the title compound.

Yield: 32 gms; Melting point: 156-160° C.; Purity by HPLC: 99.59%.

Example-15: Preparation of Amorphous (1S)-1,5-anhydro-1-[3-[[5-(4-fluorophenyl)-2-thienyl] methyl]-4-methylphenyl]-D-glucitol (Formula-1)

The mixture of dichloromethane (70 ml) and (1S)-1,5-anhydro-1-[3-[[5-(4-fluorophenyl)-2-thienyl]methyl]-4-methylphenyl]-D-glucitol (10 gms) was heated to 40-45° C. and stirred the reaction mixture for 45 minutes at the same temperature. Slowly cooled the reaction mixture to −30 to −25° C. and stirred for 10 minutes at the same temperature. n-heptane (400 ml) was added to the reaction mixture at −30 to −25° C. and stirred for 30 minutes at the same temperature. Filtered the precipitated solid and dried to get the title compound. Yield: 9.0 gms.

The P-XRD pattern of the obtained compound was depicted in FIG. 1.

Example-16: Preparation of Crystalline Form-M of (1S)-1,5-anhydro-1-[3-[[5-(4-fluoro phenyl)-2-thienyl]methyl]-4-methyl phenyl]-D-glucitol (Formula-1)

(1S)-1,5-anhydro-1-[3-[[5-(4-fluorophenyl)-2-thienyl]methyl]-4-methylphenyl]-D-glucitol (5.0 gms) was dissolved in acetone (40.0 ml) at 25-30° C. and stirred for 15 minutes at the same temperature. The above reaction mixture was slowly added to n-heptane at 25-30° C. and further stirred for 15 minutes at the same temperature. Filtered the precipitated solid and dried to get the title compound. Yield: 3.85 gms.

The P-XRD pattern of the obtained compound was depicted in FIG. 3.

Example-17: Preparation of (1S)-1,5-anhydro-1-[3-[[5-(4-fluorophenyl)-2-thienyl]methyl]-4-methyl phenyl]-D-glucitol in Combination with HPC (Formula-1)

Methanol (2.5 ml) was added to (1S)-1,5-anhydro-1-[3-[[5-(4-fluorophenyl)-2-thienyl]methyl]-4-methylphenyl]-D-glucitol (5 gms) at 25-30° C. and stirred for 15 minutes at the same temperature. Heated the reaction mixture to 40-45° C. Slowly added HPC {HPC (5 gms) in 2.5 ml of methanol} solution to the reaction mixture at 40-45° C. and stirred for 10 minutes at the same temperature. Distilled off the solvent completely from the reaction mixture under reduced pressure to provide the title compound. Yield: 2.5 gms.

Figure 4:
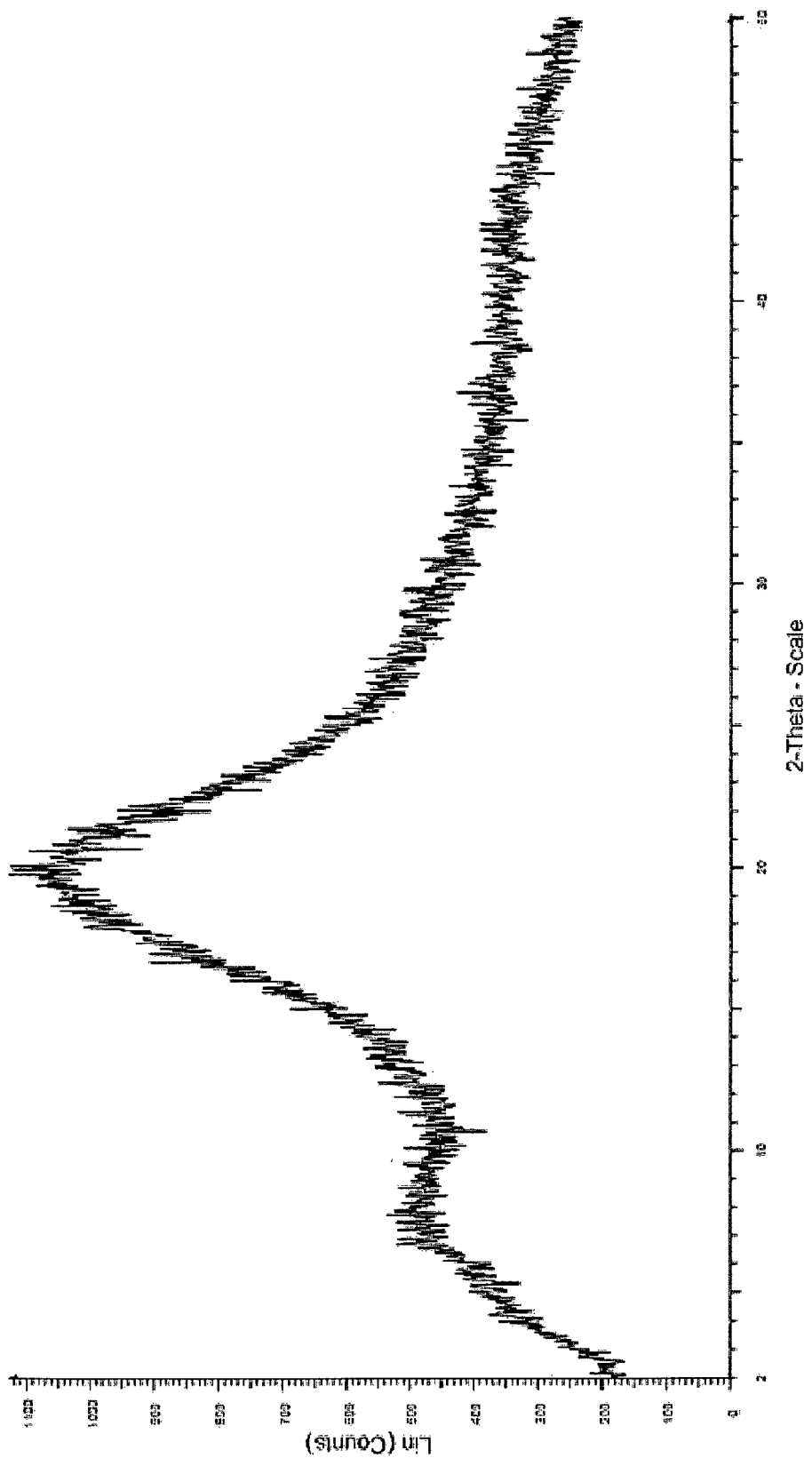
FIG. 4: Illustrates the PXRD pattern of amorphous solid dispersion of (1S)-1,5-anhydro-1-[3-[[5-(4-fluorophenyl)-2-thienyl]methyl]-4-methylphenyl]-D-glucitol compound of formula-1.

The P-XRD pattern of the obtained compound was depicted in FIG. 4.

Example-18: Preparation of (1S)-1,5-anhydro-1-[3-[[5-(4-fluorophenyl)-2-thienyl]methyl]-4-methyl phenyl]-D-glucitol in Combination with HPC (Formula-1)

Dichloromethane (30 ml) was added to (1S)-1,5-anhydro-1-[3-[[5-(4-fluorophenyl)-2-thienyl]methyl]-4-methylphenyl]-D-glucitol (250 gms) at 25-30° C. and stirred for 15 minutes at the same temperature. Heated the reaction mixture to 40-45° C. Slowly added HPC solution (250 gms of HPC in 30 ml of dichloromethane) to the reaction mixture at 40-45° C. and stirred for 10 minutes at the same temperature. Distilled off the solvent completely from the reaction mixture under reduced pressure to provide the title compound. Yield: 100 gms.

The P-XRD pattern of the obtained compound was depicted in FIG. 4.

We claim:
1. A process for the preparation of amorphous form of (1S)-1,5-anhydro-1-[3-[[5-(4-fluorophenyl)-2-thienyl]methyl]-4-methylphenyl]-D-glucitol compound of formula-1,

Formula-1

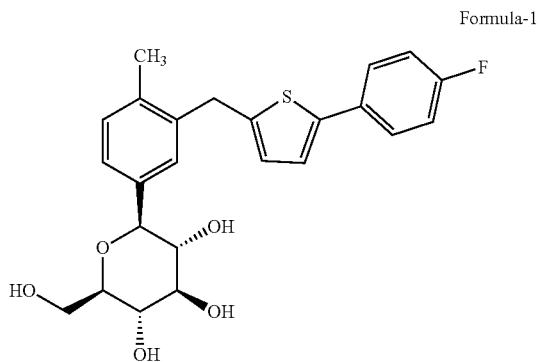 [SMILES: Cc1ccc([C@@H]2O[C@H](CO)[C@@H](O)[C@H](O)[C@H]2O)cc1Cc1ccc(-c2ccc(F)cc2)s1]

comprising:
 a) treating (2R,3R,4R,5S,6S)-2-(acetoxymethyl)-6-(3-((5-(4-fluorophenyl) thiophen-2-yl) methyl)-4-methylphenyl)tetrahydro-2H-pyran-3,4,5-triyltriacetate compound of formula-6

Formula-6

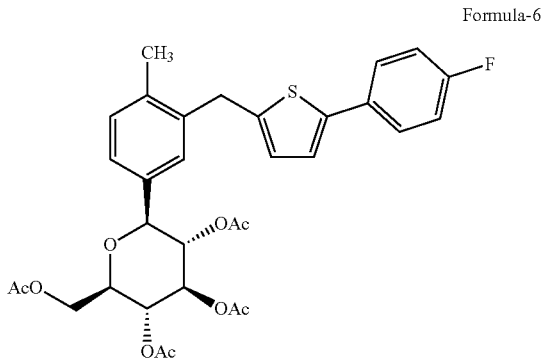 [SMILES: CC(=O)OC[C@H]1O[C@@H](c2ccc(C)c(Cc3ccc(-c4ccc(F)cc4)s3)c2)[C@H](OC(C)=O)[C@@H](OC(C)=O)[C@@H]1OC(C)=O]

with a base in a solvent,
 b) absorbing the obtained compound on silica gel or silicon dioxide or neutral alumina,
 c) adding a solvent, and
 d) obtaining amorphous form of compound of formula-1.

2. The process according to claim 1, wherein
the base is an organic base or an inorganic base; and the solvent is selected from the group consisting of alcohol solvents, ether solvents, chloro solvents, ketone solvents, ester solvents, hydrocarbon solvents, polar aprotic solvents, polar solvents, and a mixture thereof.

3. The process according to claim 1, wherein the process for the preparation of compound of formula-6 comprises:
 a) reacting (3R,4S,5R,6R)-3,4,5-tris(trimethylsilyloxy)-6-((trimethylsilyloxy)methyl) tetrahydro-2H-pyran-2-one compound of formula-3

Formula-3

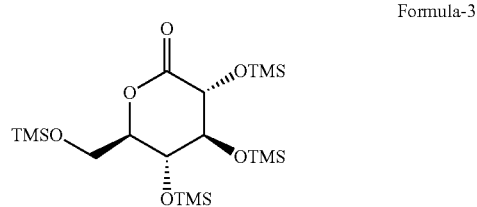

with 2-(4-fluorophenyl)-5-(5-iodo-2-methylbenzyl) thiophene compound of formula-4

Formula-4

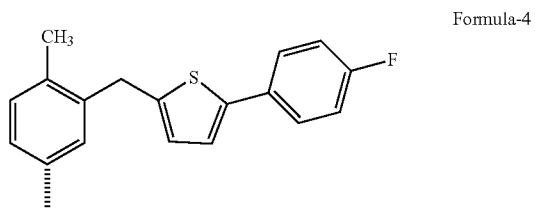

in presence of 1.0 to 4.0 mole equivalents of alkyl lithium with respect to compound of formula-3 in a solvent, at a temperature ranging from -78° C. to 0° C., wherein the alkyl lithium is added to a mixture of the compound of formula-3 and the compound of formula-4, to obtain (2S, 3R,4S, 5S, 6R)-2-(3-((5-(4-fluorophenyl) thiophen-2-yl)methyl)-4-methylphenyl)-6-(hydroxymethyl)tetrahydro-2H-pyran-2,3,4,5-tetraol compound of formula-5, Formula-5

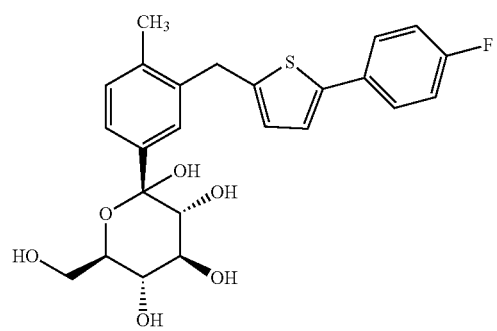

b) reducing the compound of formula-5 with a reducing agent in a solvent to obtain compound of formula-1,
 c) acetylating the compound of formula-1 with an acetylating agent in presence of a base in a solvent to obtain compound of formula-6, and
 d) optionally purifying the compound of formula-6.

4. The process according to claim 1, wherein the compound of formula-1 is substantially free of acetyl impurity; methyl impurity; 3-acetyl impurity; iodo impurity as measured by HPLC.

5. The process according to claim 1, wherein the compound of formula-1 has an alpha isomer impurity of less than 0.1%.

6. The process according to claim 1, wherein the compound of formula-1 has a purity greater than 99.95% as measured by HPLC.

7. The process according to claim 1, wherein the compound of formula-1 has a particle size distribution of $D_{90}$ less than 150 μm.

8. The process according to claim 1, wherein the compound is absorbed on silica gel.

9. The process according to claim 1, wherein the solvent in step (c) is selected from the group consisting of methanol, water, and a mixture thereof.

10. The process according to claim 3, wherein the alkyl lithium is n-butyl lithium or methyl lithium.

11. The process according to claim 3, wherein solvent in step-a) is tetrahydrofuran, reducing agent in step-b) is triethylsilane/BF3-etherate, acylating agent for acylating the compound of formula-1 is acetic anhydride in presence of dimethyl amino pyridine and solvent in step-b) and step-c) is dichloromethane.

\* \* \* \* \*